United States Patent
Nicastro et al.

(10) Patent No.: US 10,751,283 B2
(45) Date of Patent: *Aug. 25, 2020

(54) LIPOSOMAL REHYDRATION SALT FORMULATION AND ASSOCIATED METHODS OF USE

(71) Applicant: CAPABILITY BUILDING, INC., Miami, FL (US)

(72) Inventors: Alcides Nicastro, Santa Fe (AR); Gustavo M. Souss, Miami, FL (US)

(73) Assignee: CAPABILITY BUILDING, INC., Miami, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 16/554,797

(22) Filed: Aug. 29, 2019

(65) Prior Publication Data
US 2020/0009051 A1    Jan. 9, 2020

Related U.S. Application Data

(63) Continuation-in-part of application No. 15/797,031, filed on Oct. 30, 2017, now abandoned, which is a
(Continued)

(30) Foreign Application Priority Data

Jan. 14, 2014  (AR) .......................... P20140100123

(51) Int. Cl.
*A61K 9/127* (2006.01)
*A61K 47/02* (2006.01)
(Continued)

(52) U.S. Cl.
CPC .............. *A61K 9/127* (2013.01); *A61K 47/02* (2013.01); *A61K 47/22* (2013.01); *A61K 47/26* (2013.01); *B82Y 5/00* (2013.01)

(58) Field of Classification Search
CPC ........ A61K 9/127; A61K 47/26; A61K 47/22; A61K 47/02; A61K 9/0095; B82Y 5/00; A23L 2/00
See application file for complete search history.

(56) References Cited

U.S. PATENT DOCUMENTS 7,901,708 B2   3/2011  MacLachlan et al.
10,238,687 B2  3/2019  Nicastro et al.
(Continued)

FOREIGN PATENT DOCUMENTS

WO   2004002453   1/2004
WO   2015107241   7/2015

OTHER PUBLICATIONS

Dua et al., "Liposome: Methods of Preparation and Applications," International Journal of Pharmaceutical Studies and Research, vol. III, Issue II, Apr.-Jun. 2012; pp. 14-20.
(Continued)

*Primary Examiner* — Gollamudi S Kishore
(74) *Attorney, Agent, or Firm* — Allen, Dyer, Doppelt + Gilchrist, P.A.

(57) ABSTRACT

A shelf stable liposomal based oral rehydration formulation as a mixture has an improved beverage rehydration index performance. The liposomal rehydration salt formulation prevents severe dehydration, maintains body electrolytes and fluids in a human, and rehydrates a human. The formulation includes less than 0.4% phospholipids, having an average size less than 270 nm and an osmolality of about 200 mOsm/kg.

19 Claims, 6 Drawing Sheets

Related U.S. Application Data continuation-in-part of application No. 15/111,485, filed as application No. PCT/ES2015/070003 on Jan. 7, 2015, now abandoned.

(51) Int. Cl.

| | |
|---|---|
| *A61K 47/22* | (2006.01) |
| *A61K 33/14* | (2006.01) |
| *A23L 2/74* | (2006.01) |
| *A23L 2/52* | (2006.01) |
| *A61K 47/26* | (2006.01) |
| *B82Y 5/00* | (2011.01) |

(56) References Cited

U.S. PATENT DOCUMENTS

| | | |
|---|---|---|
| 2002/0150981 A1 | 10/2002 | Canfield |
| 2005/0000868 A1 | 1/2005 | Weigel et al. |
| 2005/0008685 A1 | 1/2005 | Mitchell et al. |
| 2009/0017167 A1 | 1/2009 | Krumhar et al. |
| 2010/0267806 A1 | 10/2010 | Bumcrot et al. |
| 2016/0331778 A1 | 11/2016 | Nicastro et al. |
| 2018/0021372 A1 | 1/2018 | Nicastro et al. |
| 2018/0049983 A1 | 2/2018 | Nicastro et al. |

OTHER PUBLICATIONS

Crowe et al., "Preservation of Dry Liposomes Does Not Require Retention of Residual Water," Proceedings of the National Academy of Sciences of the United States of America, vol. 84, Mar. 1987; pp. 1537-1540.

Sun et al., "Stability of Dry Liposomes in Sugar Glasses," Biophysical Journal, vol. 70, Apr. 1996; pp. 1769-1776.

About the Asian Conference on Diarrheal Disease and Nutrition (ASCODD) particularly Bardhan et al., "Clinical Trial of Liposome-Based Oral Rehydration Solution (ORS) in Children with Acute Watery Diarrhoea," at p. 14, PIDSP J., 13 (Suppl.1); (2012); pp. 2-23.

Bardhan et al., "Absorption of Water and Electrolytes from a Liposomal Oral Rehydration Solution: An in Vivo Perfusion Study of Rat Small Intestine," ICDDR,B: Centre for Health and Population Research, GPO Box 128, Dhaka 1000, Bangladesh; (2003); 5 pages.

Bardhan et al., "Absorption of Water and Electrolytes from a Liposomal Oral Rehydration Solution (ORS): An In Vivo Perfusion Study in Rat Small Intestine," PowerPoint Presentation; (2003); 13 pages.

Bardhan et al., "Absorption of Water From a Liposomal Oral Rehydration Solution: An In Vivo Perfusion Study of Rat Small Intestine Exposed to Cholera Toxin," AGA Abstracts, Gastroenterology, 142(5) (Suppl. 1): S-21 (2012).

Bardhan et al., Clinical Trial of Liposome-Based Oral Rehydration Solution (ORS) in Children with Acute Watery Diarrhoea, Powerpoint Presentation; (2016); 15 pages.

Bardhan et al., Liposome-Based Oral Rehydration Solution (ORS) in Children with Acute Watery Diarrhoea: An Exploratory Clinical Trial; (2016); 11 pages.

International Search Report and Written Opinion (translation), International Application No. PCT/ES2015/070003, dated Mar. 24, 2015; 17 pages.

Lakougna, H., "Enteric and Diarrheal Diseases: Landscape Analysis of the Technologies used to Prevent, Diagnose, and Treat Pediatric Cases," Path (NGO); (2016); 29 pages.

Pizarro et al., "Rice-Based Oral Electrolyte Solutions for the Management of Infantile Diarrhea," N. Engl. J. Med. 324:517-521 (1991).

Review Proposal Consultation Document, "Review of Clinical Guideline (CG84)—Diarrhoea and Vomiting Caused by Gastroenteritis: Diagnosis, Assessment and Management in Children Younger Than 5 Years," National Institute of Health and Clinical Excellence; (2012); 38 pages.

UNICEF/WHO, "New Formulation of Oral Rehydration Salts (ORS) with Reduced Osmolarity," World Health Organization, Dept. of Child and Adolescent Health and Development, Technical Bulletin No. 9; (2001); 3 pages.

Wapnir et al., "Oral Hydration Solutions in Experimental Osmotic Diarrhea: Enhancement by Alanine and Other Amino Acids and Oligopeptides," Am. J. Clin. Nutr. (1988); 48:84-90.

Wapnir et al., "Improved Water and Sodium Absorption from Oral Rehydration Solutions Based on Rice Syrup in a Rat Model of Osmotic Diarrhea," J. Pediatr. (1991).; 118:S53-61.

Faruqui et al., "Perfusion Study on Rat Small Intestine Exposed to Cholera Toxin to Observe Absorption of Water and Electrolytes from a Liposome Based ORS," Journal of Parasitic Diseases: Diagnosis and Therapy, vol. 1, No. 1; 2016; pp. 1-10.

Elliott, "Acute Gastroenteritis in Children," BMJ; Jan. 6, 2007; vol. 334; pp. 35-40.

Steiner et al., "Is This Child Dehydrated?" JAMA; Jun. 9, 2004; vol. 291, No. 22; pp. 2746-2754.

Anonymous, "Burden of Norovirus Illness in the U.S.," Center for Disease Control (CDC); downloaded from the Internet on Aug. 27, 2019; https://www.cdc.gov/norovirus/trends-outbreaks/burden-US.html; 1 page.

LIPOSOMAL REHYDRATION SALT FORMULATION AND ASSOCIATED METHODS OF USE

PRIORITY APPLICATION(S)

This is a continuation-in-part application of U.S. patent application Ser. No. 15/797,031 filed Oct. 30, 2017, which is a continuation-in-part application of U.S. patent application Ser. No. 15/111,485 filed Jul. 14, 2016, which is based upon a U.S. national stage application as international application No. PCT/ES2015/070003 filed Jan. 7, 2015, which claims priority from Argentina patent application No. P20140100123 filed Jan. 14, 2014, the disclosures which are hereby incorporated by reference in their entirety.

FIELD OF THE INVENTION

The present invention relates to the field of improved, liposome based, oral rehydration salts ("ORS") with improved oral palatability and water absorption and retention over existing commercial non-encapsulated ORS, featuring enhanced stability and characterized by an atypical manufacturing approach to production of stable liposomes containing relatively high concentrations of salts. In particular, it relates to production and commercial utility of stable, low osmolality liposome based, highly concentrated encapsulated, oral rehydration salt formulations.

STATE OF THE ART

References to oral rehydration salts in the form of liposomes are not abundant in the literature. Several attempts to develop isolated products of this kind have been disclosed, which have not been successfully commercialized.

It should be noted that U.S. Patent Publication No. 2005/0008685 (now abandoned) to Mitchell describes the use of liposomes for preparing oral rehydration salts. However, the percentage inclusion ratio of salts in the resulting liposomes described therein (salts retained within said liposomes/total salts) disclosed, is a relatively low 25%. Because the methods described by Mitchell lead to excessive free salt in the resulting ORS and despite some liposomal encapsulation of the salts that are employed, the resulting Mitchell products are relatively unacceptable to patients. Furthermore, Mitchell provides no details on the actual manufacturing methods employed to arrive at the described liposomal products, no specifications for the resulting products, no test methods related to rate of encapsulation, inadequate evidence for particle size distribution determination nor a description of the test instrument employed (those skilled in the art will recognize that particle size distribution results vary widely depending on the method of particle size distribution measurement employed) nor any product stability test methods or stability results.

On the other hand, there are several reports that suggest potential benefits of administering liposomal rehydration salts in an animal model such as in "Absorption of Water and Electrolytes from a Liposomal Oral Rehydration Solution: An in vivo Perfusion Study of Rat Small Intestine" by P. K. Bardhan, A. S. M. Hamidur Rahman, Rifaat, and D. A. Sack—ICDDR,B: Centre for Health and Population Research, GPO Box 128, Dhaka 1000, Bangladesh, published in December 2003. This document makes reference to the improved mouthfeel and improved absorption mechanism of rehydration salts due to the presence of liposomes.

Salt concentrations, as recommended by the World health organization "WHO" for rehydration salts are shown below:

| ORS | | | Concentration mmol/L | | | | |
|---|---|---|---|---|---|---|---|
| Function | Component | g/L | Glucose | Na+ | K+ | Cl− | Cit3− |
| Rehydration salts | Sodium chloride | 2.6 | | 44.5 | | 44.5 | |
| | Potassium Chloride | 1.5 | | | 20.1 | | |
| | Sodium citrate | 2.9 | | 29.6 | | | 9.9 |
| Sweetener | Glucose | 13.5 | 74.9 | | | | |

Glucose is not only a sweetener in these WHO formula requirements but also plays an active role in positively affecting salt transport in non-liposomal based ORS formulations.

SUMMARY OF THE INVENTION

Figure 1:
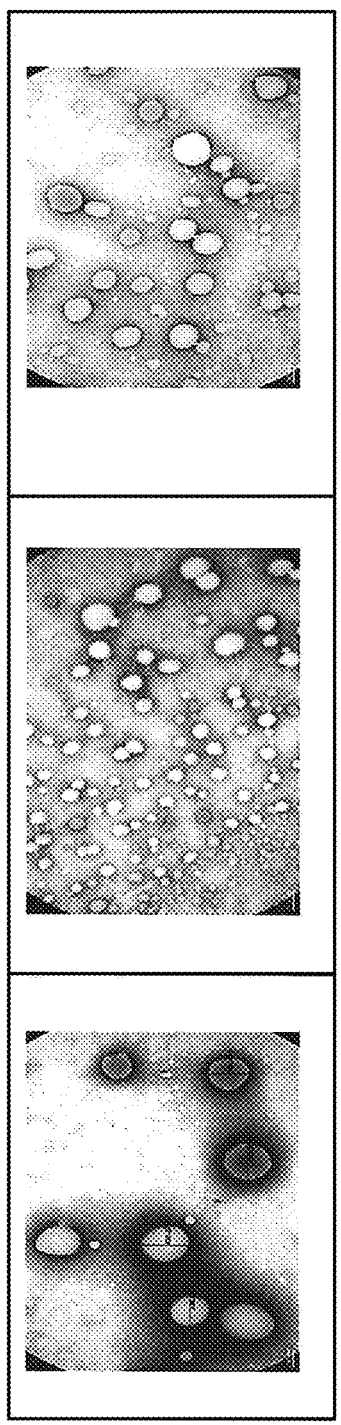
FIG. 1 shows TEM (Transmission Electron Microscopy) images of a liposome sample and disclosed in the parent application after the final stage of the preparation process.

A liposomal rehydration salt formulation comprises phospholipids at a concentration of about 1.0 g/L to 10.0 g/L, salts, water, and a percentage inclusion ratio of salts (salts retained within total salts/liposomes) of at least 50% and a sodium electrolyte of about 12 mmol/L to 90 mmol/L, wherein the formulation has an actual osmolarity lower than 130 mmol/k based on the at least 50% encapsulation of the salts and the liposomes comprise a particle diameter ranging from 200 nm to 500 nm. The sodium electrolyte may be from about 15 mmol/L to 75 mEq/L. The liposomal rehydration salt formulation may further comprise about 2 mmol/L to 25 mol/L of potassium electrolyte. The phospholipids may be selected from the group consisting of phosphatidylcholines (PCs), lyso-phosphatidylcholines (LPC), phosphatidylserines (PSs), phosphatidylethanolamines (PEs), phosphatidylglycerols (PGs), phosphatidylinositols (PIs), phosphatidic acids (PAs), and mixtures thereof. The composition may further comprise additives and antioxidants selected but not limited to the group consisting of phytosterols and their esters, tocopherol, and mixtures thereof.

The salts may be selected from the group consisting of sodium chloride at a concentration of 0.7 g/L to 2.8 g/L, potassium citrate at a concentration of 0.8 g/L to 2.5 g/L, sodium citrate at a concentration of 0.5 g/L to 2.9 g/L, and mixtures thereof. The formulation may further comprise about 5 g/L to 50 g/L of glucose and about 5.0 g/L to 15 g/L of at least one additional sugar. The formulation may further comprise Stevia at a concentration of about 0.1 g/L to 0.25 g/L. The formulation may further comprise natural flavours at a concentration of about 1 g/L to 3.5 g/L.

A method of preventing severe dehydration and maintaining body electrolytes and fluids in a human comprises orally administering a liposomal rehydration salt formulation comprising phospholipids at a concentration of about 1.0 g/L to 10.0 g/L, salts, water, and a percentage inclusion ratio of salts (salts retained within total salts/liposomes) of at least 50% and a sodium electrolyte of about 12 mmol/L to 90 mmol/L, wherein the formulation has an actual osmolarity lower between 200 and 300 mOsmol/L and at least 50% encapsulation of the salts with the liposomes comprising a relatively narrow particle size diameter ranging from 200 nm to 500 nm. The rehydration salt formulation may be formulated for oral administration for use by humans that are pregnant or breast-feeding or engaged in one or more sport exercises, outdoor activities, extreme weather activities, climbing and flying. The liposomal rehydration salt formulation may also be formulated for oral administration for use by patients having one or more gastrointestinal disorder, skin burns, parenteral or enteral nutrition ailments, celiac disorders, diabetes, SGLT2 inhibitor treatment disorders, intestinal failure, Short Bowel Syndrome, Cycling Vomiting Syndrome, Gastroparesis, Postural Orthostatic Tachycardia Syndrome, Ulcerative Colitis, Colon Cancer, Dysphagia, Sjogren Syndrome, Crohn's disease, Lupus, Alzheimer's disease, Renal complications, HIV, Inflammatory Bowel Disease, an Ostomy, Microvillus Inclusion Disease, and Cystic Fibrosis, treatment of the elderly, use in the military and in chemotherapeutic interventions involving gastric system upsets.

The sodium electrolyte may be from about 35 mmol/L to 55 mmol/L. The liposomal rehydration salt formulation may include a potassium electrolyte and administering about 15 mmol/L to 25 mmol/L of the potassium electrolyte. The liposomal rehydration salt formulation may comprise about 5 g/L to 40 g/L of glucose and 8.0 g/L to 15 g/L of at least one additional carbohydrate.

A method of rehydrating a human suffering from dehydration comprises orally administering a liposomal rehydration salt formulation comprising phospholipids at a concentration of about 1.0 g/L to 10.0 g/L, salts, water, and a percentage inclusion ratio of salts (salts retained within total salts/liposomes) of at least 50% and a sodium electrolyte of about 12 mmol/L to 90 mmol/L, wherein the formulation has an actual osmolarity lower than 200-300 mOsmol/L with at least 50% encapsulation of the salts and comprising liposomes with a particle size diameter ranging from 200 nm to 500 nm.

DETAILED DESCRIPTION

There now follows a description of the liposomal rehydration salt formulation described in the parent and grandparent '031 and '485 applications, followed by greater details of the new formulation, its manufacture, composition, and testing.

The liposomal rehydration salt formulation contains phospholipid liposomes, preferably selected from the group consisting of phosphatidylcholines (PCs), lyso-phosphatidylcholines (LPC) phosphatidylserines (PSs), phosphatidylethanolamines (PEs), phosphatidylglycerols (PGs), phosphatidylinositols (PIs), phosphatidic acids (PAs), and mixtures thereof, at a concentration of less than 6% (W/V); and optionally an additive or antioxidant selected from phytosterols and their esters, tocopherols, and mixtures thereof, at a concentration of 0.2 to 0.5% (W/V); water; salts selected from the group consisting of sodium chloride at a concentration of 0.7 to 2.8 g/l, potassium citrate at a concentration of 0.8 to 2.5 g/l, sodium citrate at a concentration of 0.5 to 2.9 g/l, and mixtures thereof; optionally, it may further comprise carbohydrates, among which glucose is preferred.

Intestinal salt absorption mechanisms are enterocyte co-transport systems. These systems involve carrying salts into the body along with other molecules, glucose being the most important among them. This is why rehydration salt formulations targeting hyponatremia, associated both with sports and acute diarrhea, are composed of a mixture of salts and glucose. Salt concentration should be higher than that of the body, so that glucose-mediated transport can be enabled by an osmotic gradient allowing for incorporation of salts through membranes. However, glucose intake is restricted by the calorie intake of this molecule.

Liposomes are nanoparticles consisting of a phospholipid bilayer, the same as cell membranes of enterocytes. Based on different mechanisms, liposomes (and all the contents carried in them) are highly capable of being absorbed by the small intestine cells, increasing bioavailability of the transported actives. Liposomal rehydration salt formulations aim at providing different electrolyte transport mechanisms than the known sugar assisted mechanisms of electrolyte salt absorption relied upon in commercially available non-liposomal oral rehydration solutions. In vivo tests have shown that an encapsulated ORS formulation having salt concentrations in accordance with WHO standards causes a 1.39-fold hydration increase in animals under normal conditions, as compared to the WHO recommended formula, and a 1.45-fold hydration increase in animals infected with cholera as compared to the WHO recommended formula ("Absorption of Water From a Liposomal Oral Rehydration Solution: an In Vivo Perfusion Study of Rat Small Intestine Exposed to Cholera Toxin" Gastroenterology—Volume 142, Issue 5, Supplement 1, Pages S-21, May 2012—Pradip K. Bardhan, Nasirul Islam, Rifat Faruqui).

In view of the above, one of the great advantages of the liposome based formulation relies on the use of far lower carbohydrate concentrations, ranging from 0 to 6 g/l, which improves mouthfeel and tolerance to the formulation and which results in lower overall osmolarity. Furthermore, it would be possible to replace glucose with a mixture of carbohydrates such as fructose, dextrose, high fructose corn syrup and mixtures thereof, and even with artificial sweeteners such as sucralose in liposome based electrolyte mixtures. Low glucose concentration is very important in ORS sport drinks and for use by diabetics. It is even possible to accomplish efficient rehydration in the absence of glucose due to the new electrolyte uptake mechanism that does not rely on carbohydrate assistance, which would allow the formulation to be consumed by diabetics.

In addition, and also due to lower glucose concentration, the formulation of the present invention exhibits reduced osmolality with respect to commercially-available formulations which accounts for the possibility of accomplishing efficient rehydration without running the risk of inducing hypernatremia in the patient.

Furthermore, one of the novel aspects of the invention is the fact that it significantly improves the percentage inclusion ratio of salts (salts retained within said liposomes/total salts) with respect to the prior art. This ratio is at least 40%, preferably at least 50%, more preferably at least 60%. In a preferred embodiment, the percentage inclusion ratio is at least 56%. These high inclusion ratio values have not been previously disclosed in the prior art, and therefore allow for the preparation of formulations containing lower free salt concentrations with improved rehydration effects as disclosed. This high inclusion ratio was achieved by using a unique tangential ultrafiltration method, but improved manufacturing techniques have now been established. Although well-known, this method has never been employed to increase the ratio of oral rehydration salts encapsulated within liposomes to the total amount of the salts of the invention, thereby solving the technical problem of rejection caused by oral rehydration salts due to their unpleasant taste.

It has been demonstrated in Example 3 that liposomal encapsulation of more than 50% of the electrolyte salts in the formulation causes the unpleasant taste inherently associated with the commercially available non-liposomal free electrolyte salts, to be almost completely absent. This improved palatability facilitates consumption by children younger than 12 years as well as adults, who represent the most affected population in terms of acute dehydration.

Figure 2:
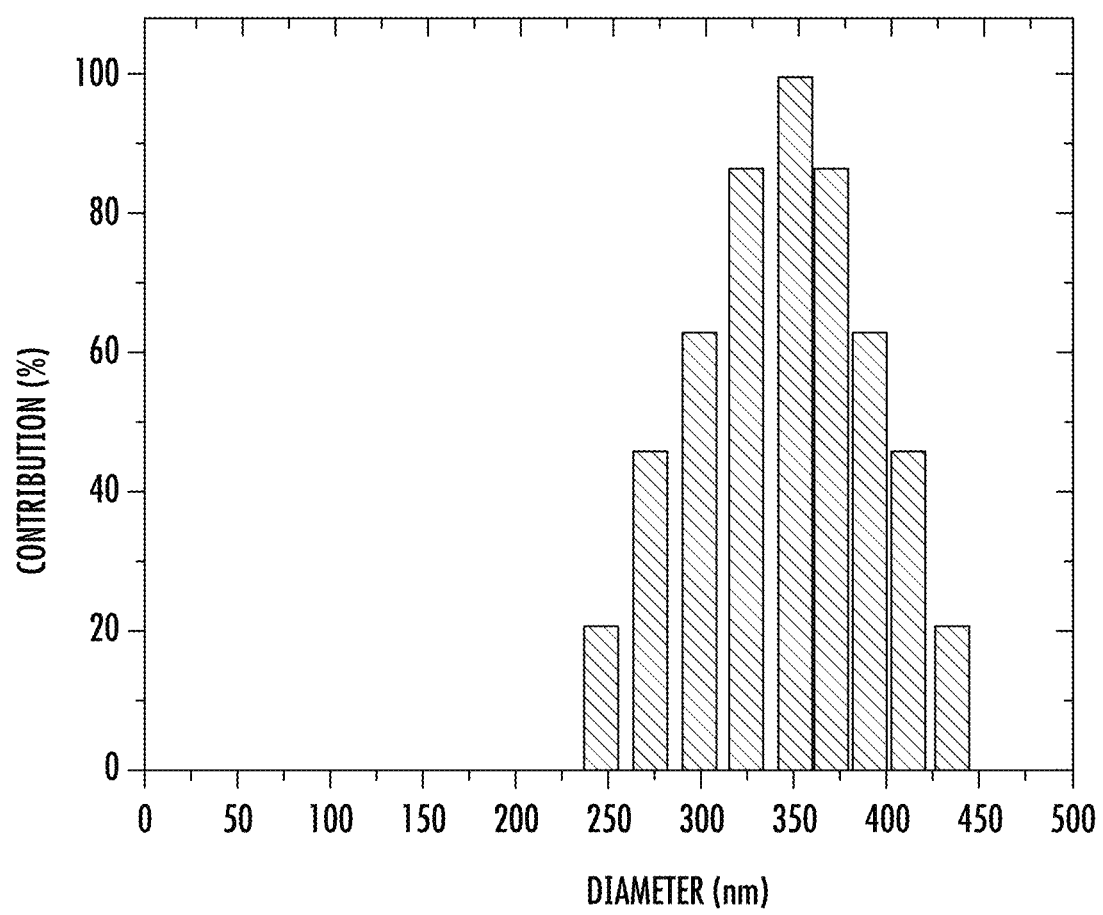
FIG. 2 illustrates the diameter distribution of the liposomes formulation as disclosed in the parent application, wherein the particle size distribution in a DLS (Dynamic Light Scattering) analysis is shown.

Furthermore, the liposomes of the formulation described in the parent and grandparent applications are produced such that the particle diameter ranges from 200 to 500 nm; preferably from 225 to 450 nm, as shown in FIG. 2.

The liposomal rehydration salt formulation is used as an orally administered mixture for replacement of fluids and electrolyte salts in the treatment of dehydration caused by diarrhea and vomiting, prevention of severe dehydration, and maintenance of body electrolytes and liquids. The formulation may also be an oral administration infusion for use in sport activities.

The process for preparing the formulation described in the parent and grandparent applications comprises the following steps:

a. preparing an aqueous phase (AP) or buffer solution comprising sodium chloride, potassium citrate, sodium citrate dissolved in distilled water;

b. separately preparing an ethanol phase (EP), by dissolving the phospholipid at a concentration of 0.1 to 6% (W/V), and optionally an antioxidant at a concentration of 0.2 to 0.5% (W/V) in alcohol, preferably ethyl alcohol;

c. inducing formation of liposomes by slowly injecting the EP into the AP at between 25 and 65 Deg. C while stirring;

d. subjecting the liposomal solution obtained in step "c" to a non-makeup based diafiltration using an ultrafilter membrane (DF) concentration process which substantially removes the free electrolytes that remain in the aqueous portion of the mixture resulting from the Step "c" mixture while maintaining the liposomes and their contents, thus reducing the volume at least by 10-fold;

e. subjecting the resulting liposomal solution obtained in step "d," which has essentially removed all non-liposomal electrolytes from the mixture, to a tangential ultrafiltration (TUF) concentration process, wherein ethanol is then eliminated and the buffer is replaced with saline solution, and maintaining the liposomes and their contents.

In step "a," the aqueous phase (AP) or buffer comprises sodium chloride at a concentration of 6 to 20 mmol/l, potassium citrate at a concentration of 1 to 12 mmol/l, sodium citrate at a concentration of 2 to 5 mmol/l, and distilled water.

In step "e" of the process, the saline solution comprises a sodium concentration of 12 to 50 mmol/l, a potassium concentration of 3 to 36 mmol/l, a chloride concentration of 15 to 40 mmol/l, a citrate concentration of 8 to 17 mmol/l, and it further comprises glucose at a concentration of 17 to 45 mmol/l.

Furthermore, the AP:EP volume ratio in step "c" is at least 10:1; preferably at least 10:0.5; more preferably at least 10:0.4.

The process step "c" comprises a perpendicular flow process, wherein the ethanol phase is added to the aqueous phase by perpendicular coupling to the flow of the former, and with a linear velocity ratio REP/RAP of no more than 1/200 to form the initial electrolyte containing liposomes.

EXAMPLES

Example 1

Preparation of the Liposomal Rehydration Salt Formulation as Described in the Parent '031 and Grandparent '485 Applications a) Preparation of the Ethanol Phase (EP)

25 g of purified soybean phosphatidylcholine and 0.5 L of ethanol are added, heated to 65° C., and stirred until completely dissolved. A total amount of 2.5 g of mixed tocopherols (ascorbyl palmitate and D-Alpha-Tocopherol) is added as antioxidant. The solution is left to rest until it reaches room temperature.

b) Preparation of the Saline Aqueous Phase (AP)

4.33 g Sodium chloride, 3.42 g Potassium citrate, and 4.83 g Sodium citrate are dissolved in 4.5 L water and stirred at room temperature until completely dissolved.

c) Production of Liposomes 0.5 L of Ethanol phase is slowly added on 4.5 L of Aqueous phase under continuous circular stirring. This may be also performed by means of a Cross-Flow or Perpendicular Flow process, wherein the Ethanol phase is added on the Aqueous phase by perpendicular coupling to the flow of the former, and with a linear velocity ratio, REP/RAP, of no more than 1/200. FIG. 1 shows liposomes formed with both processes. FIG. 2 shows the results of particle size distribution in DLS (Dynamic Light Scattering) analysis.

d) Removing Free Solution Based Electrolytes from the Mixture Resulting from Step "c"

Tangential diafiltration, without adding make-up permeate is carried out so as to remove the free electrolytes in the aqueous portion of the mixture essentially removing nearly all free electrolytes that are not trapped in the liposomes. This process is completed after removing 90% volume of the previous liposomal dispersion.

e) Buffer Substitution

Ultrafiltration by tangential flow is then carried out on the resulting mixture to remove ethanol from the liposomal salt solution. While the process is conducted, the solution is fed with makeup permeate not containing ethanol at a speed equal to the permeation speed with an aqueous solution of Sodium chloride (1.05 mg/ml), Potassium citrate (0.83 mg/ml), Sodium citrate (1.17 mg/ml) and Glucose (6.75 mg/ml) thus removing the ethanol introduced in the liposome formation Step "c" and adding the required final concentration of free electrolytes and carbohydrates to obtain the final ORS formulation.

The liposomal rehydration salt formulation described in the parent and grandparent applications is thereby obtained with the formulation having the following features:

Percentage inclusion ratio of salts (salts retained within liposomes/total salts) of 56.48%
Chloride concentration: 39.7 mmol/L
Citrate concentration: 16 mmol/L
Potassium concentration: 17.9 mmol/L
Sodium concentration: 69.7 mmol/L
Glucose concentration: 33.0 mmol/L Example 2

Process for Preparing the Formulation Described in the Parent and Grandparent Applications with a Percentage Inclusion Ratio of Salts of 56%

Stage a

A solution of 4.5 L distilled water with salts is prepared at the following concentration:

|  | Concentration (mmol/L) | | | | |
| --- | --- | --- | --- | --- | --- |
|  | Glucose | Na | K | Cl | Cit |
| Sodium chloride |  | 14.82 |  | 14.82 |  |
| Potassium citrate |  |  | 6.70 |  | 2.23 |
| Sodium citrate |  | 11.23 |  |  | 3.74 |
| Glucose | — |  |  |  |  |

Stage b

Separately, a solution of Phosphatidylcholine in 500 ml of 5% ethyl alcohol (W/V) is prepared.

Stage c

Formation of liposomes is induced by injecting the ethanol solution into the aqueous phase while stirring. Then 15% of the salts are encapsulated; therefore, internal and external salt concentrations are as follows:

|  | Internal | External |
| --- | --- | --- |
| Na | 3.91 | 22.14 |
| K | 1.00 | 5.70 |
| Cl | 2.23 | 12.60 |
| Cit | 0.895 | 5.074 |
| Glucose | 0 | 0 |

Stage d

Five (5) liters of liposomal ORSs are subjected to a tangential diafiltration process allowing removal of the free electrolyte solution without eliminating the damaging the liposomes and their contents. This process is performed until the volume is reduced by 10-fold. At the end of the process, 500 ml of liposomal salts having the following concentration is obtained.

|  | Internal | External |
| --- | --- | --- |
| Na | 39.1 | 22.14 |
| K | 10.0 | 5.70 |
| Cl | 22.3 | 12.60 |
| Cit | 8.95 | 5.074 |
| Glucose | 0 | 0 |

Stage e

At this stage, the buffer is substituted by using a tangential ultrafiltration process where makeup permeate volume is employed. In this case, the total volume is reduced by ten-fold, and replaced with an aqueous solution with the following salt concentration.

|  | Concentration (mmol/L) |
| --- | --- |
| Na | 31.57 |
| K | 8.13 |
| Cl | 17.96 |
| Cit | 7.24 |
| Glucose | 40.70 |

Accordingly, 500 ml of a solution of liposomal ORSs having the following salt concentration is obtained.

|  | Internal | External | TOTAL |
| --- | --- | --- | --- |
| Na | 39.1 | 30.64 | 69.74 |
| K | 10.0 | 7.88 | 17.88 |
| Cl | 22.3 | 17.45 | 39.75 |
| Cit | 8.95 | 7.02 | 15.97 |
| Glucose | 0 | 33.03 | 33.03 |

The formulation as obtained exhibits a salt concentration equal to that of the formulation recommended by the WHO, with an encapsulation efficiency of about 56.05%. Other features recommended by the WHO and UNICEF in their joint statement issued in May 2004 and accomplished in this invention are reduced glucose content and lower osmolality.

The liposomal rehydration salt formulation is thereby obtained as described in the parent and grandparent applications, the formulation having the following features:

Percentage inclusion ratio of salts (salts retained within liposomes/total salts) of 56.05%
Chloride Concentration: 39.75 mmol/l
Citrate Concentration: 15.97 mmol/l
Potassium Concentration: 17.88 mmol/l
Sodium Concentration: 69.74 mmol/l
Glucose Concentration: 33.03 mmol/l The formulation was subjected to a modified diafiltration process wherein no permeate makeup is employed using a hollow fiber cartridge with a 300 KD cut off, without feedback. Ultrafiltration continued until reducing the volume by ten-fold. This was the process as described in the parent and grandparent applications in order to obtain higher encapsulation efficiency.

Samples are taken from both final solutions.

Then, 10 ml of each formulation is taken and tangential ultrafiltered with permeate addition by using the same system but feeding back each formulation with 126 mM sucrose aqueous buffer. Thus, the sulphate ions non-encapsulated into liposomes are eliminated from each solution and substituted with a solution having the same osmolality in order to ensure integrity of the liposomal membranes.

Then 5 ml of each formulation is taken before and after the ultrafiltration process, and 10% surfactant Triton X-100 is added to each of them, in order to break the lipid membranes. This solution is kept under stirring at 25° C. for 1 hour.

Example 3

Multicenter, Randomized and Single-Blind Mouthfeel Assay

Liposomal Rehydration Salts as Described in the Parent and Grandparent Applications Samples:

Formula A: Liposomal rehydration salt formulation of the example described above.

Formula B: Liposomal rehydration salts according to example 3 of U.S. Patent Publication No. 2005/0008685 A1 to Mitchell.

Methodology

Healthy individuals from 21 to 40 years of age were recruited. Those individuals with cardiac or renal diseases, diabetics, individuals who had suffered from diarrhea the month prior to the assay, individuals affected by rhinitis, or individuals under antibiotic or iron treatment were excluded from the assay.

The screening of the individuals took place in four different shopping malls in the city of Santa Fe, Argentina. After explaining the test to the individuals and having them signed their consent (either by themselves or by their parents or legal guardians in case of underage people), the individuals were randomized. Randomization indicates the order in which the two formulations would be tasted. In order to get familiar with this type of flavors, the individuals took a little sip of the two formulations and then rinsed their mouths with water and a piece of salt-free bread. Thereafter, they tasted the two formulations in the order indicated by randomization, and they were asked to indicate the formulation of their preference. The same test was repeated twice with both formulations, after a new mouth rinse with water and pieces of bread. They were offered each formulation in amounts of less than 20 ml in total, inside red plastic glasses (to avoid color influence on the decision). The formulations were administered at room temperature, without any refrigeration.

Each individual tasted both formulations repeatedly (twice the first tasting and twice the second tasting); to corroborate consistency both times each tasting took place, kappa(k) statistic was used (URL: www.graphpad.com/quickcalcs/kappa2.cfm) as well as a 95% CI.

Results 120 individual were studied out of which 4 individuals did not meet the inclusion criteria (out of age), so the final test cohort consisted of 116 individuals with an average of 30-32 years old. The distribution of the individuals per shopping mall was similar: between 27 and 30 per each shopping mall. 59 individuals were female (50.9%).

Regarding the results obtained, we found very high consistency between the scores of the 2 tests with the same formulations, both in the first tasting (k=0.91; 95% CI: 0.85-0.98), and the second tasting (k=0.87; 95% CI: 0.80-0.94). Therefore, in the statistical analysis, it was decided to use the results corresponding to the second time each of the two tastings was scored.

Out of the 116 individuals, 97 individuals preferred the taste of the instant invention (formula A), while only 2 preferred the taste of formula B (Mitchell prior art). 17 individuals were not certain as to which they preferred, so they were not counted.

Example 4

Process for Preparing the Formulation with a Percentage Inclusion Ratio of Salts of 56% (for Sport Activities) as Described in the Parent and Grandparent Applications Stage a A solution of 4.5 L distilled water is prepared with salts at the following concentration:

| | Concentration (mmol/L) | | | | |
|---|---|---|---|---|---|
| | Glucose | Na | K | Cl | Cit |
| Sodium chloride | | 6.01 | | 6.01 | |
| Potassium citrate | | | 3.86 | | 1.29 |
| Sodium citrate | | 6.02 | | | 2.01 |
| Glucose | — | | | | |

Stage b

On the other hand, a solution of phosphatidylethanolamine in 500 ml of 4% Ethyl Alcohol (W/V) is prepared.

Stage c

Liposome formation is induced by injecting the ethanol solution into the aqueous phase while stirring. Here, 15% of the salts are encapsulated. Therefore, the internal and external salt concentrations are the following:

| | Internal | External |
|---|---|---|
| Na | 1.57 | 10.46 |
| K | 0.50 | 3.36 |
| Cl | 0.78 | 5.23 |
| Cit | 0.49 | 2.81 |
| Glucose | 0 | 0 |

Stage d

The Five (5) liters of liposomal ORSs are subjected to a diafiltration without makeup as in Example 1 to concentrate the liposomes while removing the free solution based electrolytes. This process allows for removing the buffer without eliminating or damaging the liposomes and their contents. This process is carried out until reducing the volume by 10-fold. At the end of the process, 500 ml liposomal salts having the following concentration are obtained.

| | Internal | External |
|---|---|---|
| Na | 15.7 | 10.56 |
| K | 5.04 | 3.46 |
| Cl | 7.84 | 5.23 |
| Cit | 4.90 | 2.81 |
| Glucose | 0 | 0 |

Stage e

At this stage, buffer substitution is performed, and tangential ultrafiltration with make-up permeate was employed as in example 1 t the resulting mixture. In this case, the total volume is reduced by 10-fold and replaced with an aqueous solution having the following salt concentration:

| | Concentration (mmol/L) |
|---|---|
| Na | 12.56 |
| K | 3.65 |
| Cl | 5.65 |
| Cit | 3.04 |
| Glucose | 17.80 |

This buffer further contains Stevia (Reb A 97-PureCircle) at a concentration of 0.15 g/L; Sucrose at a concentration of 28.5 g/L; Citric Acid at a concentration of 3.6 g/L; and Natural Flavors at a concentration of 1.5 g/L.

Accordingly, 500 ml of a liposomal ORS solution is obtained, containing 40 g/l phospholipid, with the following salt concentration:

| | Internal | External | TOTAL |
|---|---|---|---|
| Na | 15.7 | 12.35 | 28.05 |
| K | 5.04 | 3.62 | 8.66 |
| Cl | 7.84 | 5.61 | 13.45 |
| Cit | 4.90 | 3.02 | 7.92 |
| Glucose | 0 | 16.02 | 16.02 |

The formulation of the present example is useful for people in need of hydration due to sun exposure, illness, pregnancy, travel fatigue, hangover, mental stress, strenuous work, or just living an active life. It may be produced with orange, strawberry, apple, pear, blueberry, raspberry flavors, among others.

Example 5

Process for Preparing the Formulation with a Percentage Inclusion Ratio of Salts of 56% as Described in the Parent and Grandparent Applications Pediatric Rehydration Formulation Stage a A solution of 4.5 L distilled water is prepared with salts at the following concentration:

| | Concentration (mmol/L) | | | | |
|---|---|---|---|---|---|
| | Glucose | Na | K | Cl | Cit |
| Sodium chloride | | 14.82 | | 14.82 | |
| Potassium citrate | | | 6.70 | | 2.23 |
| Sodium citrate | | 11.23 | | | 3.74 |
| Glucose | — | | | | |

Stage b

On the other hand, a solution of phosphatidylserine in 500 ml of 3% Ethyl alcohol (W/V) is prepared.

Stage c

Liposome formation is induced by injecting the ethanol solution into the aqueous phase while stirring. Here, 15% of the salts are encapsulated. Therefore, the internal and external salt concentrations are the following:

| | Internal | External |
|---|---|---|
| Na | 3.91 | 22.14 |
| K | 1.00 | 5.70 |
| Cl | 2.23 | 12.60 |
| Cit | 0.895 | 5.074 |
| Glucose | 0 | 0 |

Stage d

The Five (5) liters of Liposomal ORSs are subjected to a diafiltration without permeate make-up to concentrate the resulting liposomes essentially free from external electrolyte salts. This process allows for removing the buffer without eliminating the liposomes and their contents. This process is carried out until the volume is reduced by 10-fold. At the end of the process 500 ml of liposomal salts having the following concentration is obtained.

| | Internal | External |
|---|---|---|
| Na | 39.1 | 22.14 |
| K | 10.0 | 5.70 |
| Cl | 22.3 | 12.60 |
| Cit | 8.95 | 5.074 |
| Glucose | 0 | 0 |

Stage e

At this stage, buffer substitution is carried out, again but this time tangential ultrafiltration is employed with permeate make-up to obtain the final ORS formulation. In this case, the total volume is reduced by 10-fold and replaced with an aqueous solution having the following salt concentration:

| | Concentration (mmol/L) |
|---|---|
| Na | 31.57 |
| K | 8.13 |
| Cl | 17.96 |
| Cit | 7.24 |
| Glucose | 40.70 |

This buffer further contains Sucralose at a concentration of 0.12 g/L; high fructose corn syrup (55° Brix) at a concentration of 33.3 g/L; Citric Acid at a concentration of 4.0 g/L; and Natural Flavors at a concentration of 1.7 g/L.

Accordingly, 500 ml of a liposomal ORS solution with 30 g/l phosphatidylserine and the following salt concentration is obtained:

| | Internal | External | TOTAL |
|---|---|---|---|
| Na | 39.1 | 30.64 | 69.74 |
| K | 10.0 | 7.88 | 17.88 |
| Cl | 22.3 | 17.45 | 39.75 |
| Cit | 8.95 | 7.02 | 15.97 |
| Glucose | 0 | 33.03 | 33.03 |

The formulation of the present example is useful for children suffering from vomiting or diarrhea under the risk of dehydration, and it may be produced with orange, strawberry, apple, pear, blueberry, raspberry flavors, among others.

Example 6

Process for Preparing the Formulation with a Percentage Inclusion Ratio of Salts of 56% for Sports Applications as Described in the Parent and Grandparent Applications Stage a A solution of 4.5 L distilled water is prepared with salts at the following concentration:

|  | Concentration (mmol/L) | | | | |
| --- | --- | --- | --- | --- | --- |
|  | Glucose | Na | K | Cl | Cit |
| Sodium chloride |  | 6.01 |  | 6.01 |  |
| Potassium citrate |  |  | 3.86 |  | 1.29 |
| Sodium citrate |  | 6.02 |  |  | 2.01 |
| Glucose | — |  |  |  |  |

Stage b

On the other hand, a solution of Phosphatidylcholine in 500 ml of 5% Ethyl alcohol (W/V) is prepared.

Stage c

Liposome formation is induced by injecting the ethanol solution into the aqueous phase while stirring. Here, 15% of the salts are encapsulated. Therefore, the internal and external salt concentrations are the following:

|  | Internal | External |
| --- | --- | --- |
| Na | 1.57 | 10.46 |
| K | 0.50 | 3.36 |
| Cl | 0.78 | 5.23 |
| Cit | 0.49 | 2.81 |
| Glucose | 0 | 0 |

Stage d

The five (5) liters of Liposomal mixture are subjected to a diafiltration without added permeate makeup as in example 1 to obtain liposomes essentially free of external soluble electrolytes. This process allows for removing the buffer without eliminating the liposomes and their contents. This process is carried out until the volume is reduced by 10-fold. At the end of the process, 500 ml of liposomal salts having the following concentration is obtained.

|  | Internal | External |
| --- | --- | --- |
| Na | 15.7 | 10.46 |
| K | 5.04 | 3.46 |
| Cl | 7.84 | 5.23 |
| Cit | 4.90 | 2.81 |
| Glucose | 0 | 0 |

Stage e

At this stage, buffer substitution is carried out followed by tangential untrafiltration with permeate make-up. per example 1 above. In this case, the total volume is reduced by 10-fold and is replaced with an aqueous solution having the following salt concentration:

|  | Concentration (mmol/L) |
| --- | --- |
| Na | 12.56 |
| K | 3.65 |
| Cl | 5.65 |
| Cit | 3.04 |
| Glucose | 17.80 |

This buffer further contains Stevia (Reb A 97-PureCircle) at a concentration of 0.13 g/L; Sucrose at a concentration of 22.2 g/L; Citric Acid at a concentration of 3.4 g/L; and Natural Flavors at a concentration of 1.5 g/L.

Accordingly, 500 ml of a liposomal ORS solution is obtained having the following salt concentration:

|  | Internal | External | TOTAL (mmol/L) |
| --- | --- | --- | --- |
| Na | 15.7 | 12.35 | 28.05 |
| K | 5.04 | 3.62 | 8.66 |
| Cl | 7.84 | 5.61 | 13.45 |
| Cit | 4.90 | 3.02 | 7.92 |
| Glucose | 0 | 16.02 | 16.02 |

This formulation may be suitable for consumption by sportspeople.

Example 7

Process for Preparing the Formulation with a Percentage Inclusion Ratio of Salts of 56% for High-Performance Sports People as Described in the Parent and Grandparent Applications Stage a A solution of 4.5 L distilled water is prepared with salts at the following concentration:

|  | Concentration (mmol/L) | | | | |
| --- | --- | --- | --- | --- | --- |
|  | Glucose | Na | K | Cl | Cit |
| Sodium chloride |  | 6.01 |  | 6.01 |  |
| Potassium citrate |  |  | 3.86 |  | 1.29 |
| Sodium citrate |  | 6.02 |  |  | 2.01 |
| Glucose | — |  |  |  |  |

Stage b

On the other hand, a solution of phosphatidylinositol in 500 ml of 5% Ethyl alcohol (W/V) is prepared.

Stage c

Liposome formation is induced by injecting the ethanol solution into the aqueous phase while stirring. Here, 15% of the salts are encapsulated. Therefore, the internal and external salt concentrations are the following:

|  | Internal | External |
| --- | --- | --- |
| Na | 1.57 | 10.46 |
| K | 0.50 | 3.36 |
| Cl | 0.78 | 5.23 |
| Cit | 0.49 | 2.81 |
| Glucose | 0 | 0 |

Stage d

The 5 Liters of resulting Liposomal mixture are subjected to a diafiltration without permeate make-up to produce essentially pure concentrated liposomes free of aqueous phase soluble electrolytes. This process allows for removing the buffer without eliminating the liposomes and their contents. This process is carried out until the volume is reduced by ten-fold. At the end of the process, 500 ml of liposomal salts having the following concentration is obtained.

|  | Internal | External |
| --- | --- | --- |
| Na | 15.7 | 10.46 |
| K | 5.04 | 3.46 |

-continued

|  | Internal | External |
|---|---|---|
| Cl | 7.84 | 5.23 |
| Cit | 4.90 | 2.81 |
| Glucose | 0 | 0 |

Stage e

At this stage, buffer substitution is carried out, using tangential ultrafiltration with permeate make-up employed. In this case, the total volume is reduced by 10-fold and replaced with an aqueous solution having the following salt concentration:

|  | Concentration (mmol/L) |
|---|---|
| Na | 12.56 |
| K | 3.65 |
| Cl | 5.65 |
| Cit | 3.04 |
| Glucose | 0 |

This buffer further contains high fructose corn syrup (55° Brix) at a concentration of 3.22 g/L; Vitamin B1 at a concentration of 0.002 g/L; Vitamin B5 at a concentration of 0.011 g/L; Vitamin B6 at a concentration of 0.011 g/L; Citric Acid at a concentration of 3.6 g/L; and Natural Flavors at a concentration of 1.5 g/L.

Accordingly, 500 ml of a liposomal ORS solution with 50 g/l phosphatidylinositol and the following salt concentration is obtained:

|  | Internal | External | TOTAL |
|---|---|---|---|
| Na | 15.7 | 12.35 | 28.05 |
| K | 5.04 | 3.62 | 8.66 |
| Cl | 7.84 | 5.61 | 13.45 |
| Cit | 4.90 | 3.02 | 7.92 |
| Glucose | 0 | 16.02 | 16.02 |

This formulation may be suitable for consumption by high-performance sports people.

Example Composition/Formulation Specifications

| Sodium | 1,035 mg/L | 45 mmol/L |
|---|---|---|
| Potassium | 782 mg/L | 20 mmol/L |
| Chloride | 1,380 mg/L | 39 mmol/L |
| Citrate | 748 mg/L | 8.7 mmol/L |
| Glucose | 13.50 g/L | 75 mmol/L |
| Total Carbohydrates | 25.5 grams |  |
| Calories | 90 |  |

In this example, based on liposome electrolyte level analysis, the actual formulation composition osmolarity would be calculated as 125.8 mmol/L based on a current theoretical osmolarity of 188, when 54% of the electrolytes are encapsulated.

These example values in the table above can vary from 5-25% and with one percent increments in the range, for example, although the greater percentage difference from the listed values is less desirable. Based on the liposome electrolytes, the actual formulation composition osmolarity should be taken as 125.8 mmol/l based on a current theoretical osmolarity of 188, with 54% of the electrolytes being encapsulated. The osmolarity analysis (meq/L) is referred to as mille-equivalents of solute per liter of solvent.

Calculated Osmolarity Analysis (meq/L)

|  | WHO 2002 | Pedialyte ® | Speedlyte ® (Inventive liposomed product) |
|---|---|---|---|
| Sodium | 75 | 45 | 45/20.2 |
| Chloride | 65 | 35 | 39/17.5 |
| Potassium | 29 | 20 | 20/9 |
| Citrate | 10 | 10 | 9/4 |
| Glucose | 75 | 139 | 75/75 |
| Total Osmolarity | 245 | 249 | 188/125.8 |

Values can vary from 5-25% for the current formulation and with one percent increments in the range, as an example.

In the human body, the amount of a substance and equivalence is a very small magnitude and it is routinely described in terms of milli-equivalents (meq) as the measure having been multiplied by 1,000. The osmolarity analysis comparing the World Health Organization 2002 standards (WHO 2002) with the formulation manufactured by Abbot as Pedialyte® and an example of the inventors' formulation described in the parent and grandparent applications, also referred to as Speedlyte®, are illustrated above and compare the example values. The Pedialyte® composition is a non-liposomal formulation that includes a number of ingredients as an oral fluid and electrolyte replacement containing no liposomes. As shown in the table, it is evident that its osmolarity is much higher than the osmolarity of the current inventive formulation. One differentiating factor in the marketplace is dramatically increased palatability and enhanced absorption efficacy driven by liposome delivery producing lower observed osmolarity of the current formulation when compared to Pedialyte. The percentage deviation ranges described above are applicable and the current formulation as shown in the tables has 45 mmol/L of sodium and 20 mmol/L of potassium from 2.28 g/L of sodium chloride plus 2.04 g/L of potassium citrate and 0.5 g/L of sodium citrate. The more important electrolyte is sodium and that can range from 12 mmol/L to as high as 90 mmol/L. Other intermediate sodium ranges have been found acceptable such as 20 to 70, 30 to 60, 35 to 55, and 40 to 50 mmol/L for the sodium. The potassium electrolytes can also vary based on the percentages described above and in one example is about 15 mmol/L to 25 mmol/L. Phospholipids help create the inventive liposomes and the resulting liposome cationic salt concentrations a range identified above of 1 to 60 g/L with other ranges as defined in the examples with 1 to 30, 1 to 40, or 1 to 50 g/L with the specific concentrations of 30, 40 and 50 g/L. The example formulation as described in the tables above has 2.5 g/L of phospholipids and that value can range from about 1 to 5 g/L, 1 to 10 g/L, in a preferred example, 5 to 10 g/L and range from 5-60 g/L, and with one percent increments in the range, for example.

The amount and type of added carbohydrates may vary and in one example, the carbohydrates are at a concentration between 6 g/L to 40 g/L. The current formulation as described in the tables has a carbohydrate concentration of 13.5 g/L of glucose and 11.5 g/L of sucrose (sugar), and in an example may range from about 8.0 g/L to about 15.0 g/L of at least one additional sugar. The level of carbohydrates may be increased to as high as 70 g/L to produce a product marketable as a mainstream product and it may be lowered to almost 0 g/L in order to meet the needs of diabetics and the elderly. Those ranges of glucose and sugar can vary from their mid-range value at 5%, 10%, 15%, 20%, and 25% differences above and below.

The size of the liposomes is important for absorption as discussed above and can vary as noted above and is preferred about at 225 to 450 nm, but can range in an example from 200 to 500 nm. Although some available commercial products have smaller sized liposomes as alleged by their manufacturers, such as 100 mm, but it has been determined their level of inclusion volume is quite low. Other oral liposome products, for example, using vitamin C, may have liposome sizes greater than 500 nm.

In the example 7 described above, natural flavors are concentrated at about 1.5 g/L. Natural flavorings and masking flavors may be at a concentration of up to 5 g/L. The example formulation has about 3.12 g/L flavorings and these values could vary from 5%, 10%, 15%, 25%, or 25% above and below those values. One example range is about 1.0 g/L to about 3.5 g/L. Stevia may be used as a natural sweetener and in example, the Stevia in the examples above is indicated at a concentration of about 0.1 to 0.2 g/L, and in the example shown in the tables, is currently about 0.15 g/L, but it is possible to go as high as 0.22 in one example. One example range is about 1.0 g/L to about 3.5 g/L.

The liposomal rehydration salt formulation not only maintains hydration, but also rehydrates those patients that are dehydrated even in cases of serious dehydration states. For example, it is possible to rehydrate a patient in need thereof while avoiding intravenous (IV) fluid salt delivery because the inventive formulation may be orally administered to humans instead of IV salt injection. The formulation also will allow overall fluid balance while avoiding the use of IV fluids. The formulation may also be used for rehydration due to stomach bugs in children and adults and for rehydration to prevent alcohol driven dehydration episodes. The liposomal rehydration salt formulation may also prevent or avoid the need for parenteral hydration, corresponding to fluids that are injected subcutaneously such as parenteral glucose or saline.

The liposomal rehydration salt formulation may be used for hydration or rehydration for pregnant or breast-feeding women and for persons that need hydration or rehydration due to exercise (sport), outdoor activities, extreme weather or high-altitude conditions, skin burns, flying, hangover episodes, diarrhea, vomiting, high fever, stomach bugs or other types of gastritis, norovirus, rotavirus, and other types of bacteria and infections leading to dehydration. Hikers that are climbing steep hills or cliffs may also find the inventive liposomal rehydration salt formulation palatable and advantageous to help in maintaining body electrolytes and proper hydration or rehydration.

The liposomal rehydration salt formulation may also be used for hydration or rehydration of different populations, including patients with parenteral and enteral nutrition, to reduce the volume of rehydration fluid and consequently the time of intravenous (IV) treatments. It may be used with celiac patients, particularly during an episode when a person has inadvertently eaten protein which they are allergic to such as found in wheat, rye, and barley which in such instances forces the body to mount an undesirable immune response leading to dehydration. The symptoms may include abdominal bloating, pain, gas, diarrhea, pale stools and weight loss. The liposomal rehydration salt formulation may also be used with elderly patients, pediatric patients, pregnant and breast-feeding patients, and diabetic patients, particularly those under a SGLT2 inhibitor treatment corresponding to a class of prescription medications that inhibit sodium-glucose transport protein 2 and that react to reduce blood glucose levels. Thus, the liposomal rehydration salt formulation can be especially effective for these types of patients. Such class of medications are sometimes referred to as gliflozin drugs that inhibit the reabsorption of glucose in the kidney and therefore lower the blood sugar, sometimes too much.

The liposomal rehydration salt formulation as described may also be used for those that suffer from intestinal absorption failure, including Short Bowel Syndrome, also called short gut, which is a malabsorption disorder caused by the lack of a functioning small intestine. Diarrhea is a typical symptom that sometimes results in dehydration, malnutrition and weight loss associated with Short Bowel Syndrome.

Other populations that will benefit from the liposomal rehydration salt formulation include those that suffer from Cycling Vomiting Syndrome (CVS) characterized by sudden, repeated episodes of severe nausea, vomiting leading to physical exhaustion that can last a few hours to several days. Persons suffering from gastroparesis which is characterized by delayed gastric emptying with paresis of the stomach, with food often remaining in the stomach for an abnormally long time, which may cause chronic nausea and vomiting in some cases with erratic blood glucose levels. Those suffering from Postural Orthostatic Tachycardia Syndrome (POTS) characterized when too little blood returns to the heart when moving from a lying down to a standing up position corresponding to orthostatic intolerance may also benefit from the liposomal rehydration salt formulation. Those suffering from ulcerative colitis and colon cancer could use the liposomal rehydration salt formulation to benefit them since often they become dehydrated.

Also, those having dysphagia and difficulty swallowing could benefit as well as those with Sjogren's syndrome, corresponding to a systemic autoimmune disease that may include dry eyes and dry mouth and often is accompanied by rheumatoid arthritis and lupus. Those with lupus or similar immune disorders may also benefit from the liposomal rehydration salt formulation. Especially beneficial would be those suffering from Crohn's Disease and lupus with typical abdominal cramping and pain as part of a chronic Inflammatory Bowel Disease (IBD) and inflammation of the digestive or gastrointestinal (GI) tract. Crohn's Disease is usually limited to the end of the small intestine, as compared to ulcerative colitis, which is usually limited to the large intestine such as the colon and rectum. The liposomal rehydration salt formulation is beneficial for sufferers of either disorder. Those having kidney disease with dangerous levels of fluid, electrolytes and waste build up will benefit from the use of the liposomal rehydration salt formulation.

Those suffering from HIV are especially benefited since often therapeutic treatment for HIV and AIDS causes vomiting and diarrhea. Diarrhea is a typical side effect that accompanies use of HIV medications used for AIDS treatment. Often this includes nausea and headache with some fever, accompanied by vomiting and diarrhea. The liposomal rehydration salt formulation is especially beneficial in this type of treatment not only to help maintain electrolytes, but for rehydration. Some antiretroviral drugs for AIDS may increase blood sugar, thus the liposomal rehydration salt formulation may be beneficial.

Those with the Inflammatory Bowel Disease (IBD) such as Crohn's Disease and ulcerative colitis would benefit as well as those with an ostomy, i.e., a stoma which is a surgically created opening between the intestines and abdominal wall, and thus typically requiring an external bag or pouch. These ostomy patients are subject to abnormal variation of glucose levels and other electrolyte changes in the body, especially in the blood and intestines. Those suffering from microvillus inclusion disease also termed Davidson's Disease also suffer from chronic, intractable diarrhea causing metabolic acidosis and severe dehydration and thus would benefit from use of the liposomal rehydration salt formulation. Those suffering from cystic fibrosis (CF) would benefit from its use. Although CF is a genetic order affecting the lungs, it may also affect the pancreas, liver, kidneys and intestines causing difficulty in breathing. It can also cause fatty stool. The liposomal rehydration salt formulation can be used in many different types of cancer treatment and especially those suffering from HIV symptoms.

The liposomal rehydration salt formulation has superior taste, higher absorption, less intake and lower sugar than other drinks and formulations not using liposomal technology. Testimonies have stated that individuals feel better hydrated after taking the disclosed liposomal rehydration salt formulation and have fewer headaches and less frequent need of IV administered fluids. Taken regularly, it especially may provide those suffering from gastroparesis, Crohn's Disease, ulcerative colitis, POTS, SBS, and colorectal cancer to reduce IV hydration and hospital visits, increase energy, reduce palpitations, feeling less thirsty, experiencing fewer headaches, eliminating cramps and reducing dizziness. It has been shown previously in an animal intestine model that the liposomal rehydration salt formulation hydrates in one-third of the time and requires only one-third of the intake when compared to many commercially available non-liposomal based hydration drinks, however unless tested in oral applications in humans, it was unknown if the animal tissue model would translate favorably in humans under oral treatment. The current liposomal formulation also uses 46% less sugar than many commercially available hydration drinks because salt absorption is enhanced instead by the liposomal delivery system instead of glucose or other sugars and because liposomal rehydration formulations have improved palatability. The current formulation aids those that live with the risk of dehydration and it is better than water since water is a very poor hydrator for moderate and severe situations and may cause loss of fluid greater than the amount of fluid consumed, thus leading to electrolyte imbalance. Even coconut water often may not contain enough electrolytes for maintaining proper hydration in severe and chronic dehydration situations. Usually, sports drinks do not contain enough electrolytes because they are designed for mild dehydration situations. The electrolyte powders and tablets that are commonly available present absorption limitations and bad taste. Many commercially available oral rehydration solutions (ORS) represent old, unsophisticated technology which causes patient compliance problems due to their highly salty taste as compared to the current liposomal rehydration salt formulation of the invention that uses nano-liposomal encapsulated electrolytes for higher fluid and electrolyte absorption, less intake requirement and far better taste acceptability by patients. The formulation can be diluted with water, juices and other drinks, depending on the electrolyte level required.

It is possible in some cases to add small amounts of other functional ingredients as part of the liposome formulation technology of the invention, including water soluble vaccines, drugs, amino acids, mineral salts, vitamins, nutraceuticals, probiotics, prebiotics, and other flavors, including nutritive and non-nutritive sweeteners either encapsulated in the liposomes or carried in the associated water phase. The amounts would vary depending on end uses.

Enhanced Formulation, its Manufacture, Plant Sterol Addition, Product Comparison with Mitchell and Testing There now follows further results of the development, testing and trials the inventors conducted for the improved formulation. The inventors found a more enhanced manufacturing process to produce a superior formulation and were better able to test against the replicated product described in the Mitchell reference for testing.

A new shelf stable liposome based oral rehydration mixture exhibiting dramatically improved Beverage Rehydration Index performance over commercially available non-liposomal electrolyte preparations in human clinical trials is described.

In the application as related to the parent and grandparent applications and which granted as commonly assigned U.S. Pat. No. 10,238,687, the inventors described a unique method for the production of a liposome based oral rehydration mixture which employed several tangential ultrafiltration steps as a means of removing essentially all of the un-encapsulated electrolytes that remained in solution from phospholipid encapsulated electrolytes. Following isolation of these essentially pure liposomes, appropriate electrolyte and buffering agents and other additives were employed to reach the desired end product. Nevertheless, the method disclosed in the granted '687 patent mentioned above is cumbersome, time consuming and therefore does not lend itself well to commercial manufacturing of a reasonably priced product. Therefore, the inventors undertook to develop a more commercially viable process for a product and to compare its physiochemical and human performance characteristics with other products, including that product disclosed by the Mitchell '685 reference.

An objective was to produce a commercially viable processes and liposomal electrolyte compositions containing shelf-stable pasteurized ready to drink (RTD) low caloric liposomal based hypotonic electrolyte oral rehydration mixtures characterized by exceptionally high loadings of electrolytes in the liposomes and having appropriate stable physiochemical properties including without limitation an appropriate particle size distribution, encapsulated electrolyte content in excess of 50%, osmolality below 400 mOsmol/L, dramatically improved patient acceptance and containing appropriate levels of electrolytes as recommended by the World Health Organization (WHO) which perform well in established clinical rehydration models such as the Beverage Rehydration Index (BHI).

New Manufacturing Process and Development of Stable Liposomal Encapsulated Electrolyte Formulations
Outer Liposome Coatings Two of the most used polymers when coating a nanoparticle to modify or change its mode of action are polyethylene glycol (PEG) and hyaluronic acid (HA). In the case of liposomes for oral use (such as liposomal electrolyte salt formulation) the coating aims to solve problems related to the stability of the resulting liposomes as they pass throughout the gastro-intestinal tract as well as to the stability and integrity of the liposomal mixture once manufactured and bottled even under prior pasteurization exposing the mixture to high temperatures. But regardless of whether or not this gastric tract transit effect is achieved, there is a lateral effect related to the adhesion of the liposomes to specific sites of the gastrointestinal tract pathway due to the coating, which must be taken into account.

In the inventive formulation now described, the inventors studied coating of liposomes with both PEG and with HA separately and their performance in relation to the same formulation without the use of such additives. In the case of coating with HA, BHI (Beverage Hydration Index) values were found experimentally to be lower than the BHI values obtained without HA incorporation. Thus HA was not used in the inventive formulation as will now be described. In attempted use of PEG as a liposomal coating, the inventors found that extreme outcomes such as very high or very low BHI values were obtained. These observations lead the inventors to believe that this coating is highly dependent on the differences in gastrointestinal lining and gastrointestinal acidity of each tested subject and thus results were highly variable between subjects. It must also be taken into consideration that the coating of liposomes with PEG increases the liposome diameter by about 100 nm. This, in turn, may decrease the liposome absorption. Thus, the experimental results led the inventors to conclude that neither PEG nor HA additives would be suitable for use in encapsulated electrolyte liposomal preparations.

Plant Sterol Addition to Liposomal Membranes

It is known that the aggregated sterols when incorporated into liposome phospholipid bilayers leads in part to a stiffening (rigidity) of the liposome. This increased rigidity reduces and can even eliminate the dynamic physical transitions of the liquid-gel interface of bilayers of pure phospholipids. This often leads to more stable physicochemical property behavior of liposomal systems. It has been shown that the overall effect of sterols incorporated into liposomal bilayers can provide improved liposomal stability against several different factors including but not limited to temperature, pH, ionic strength, detergents. However, not all sterol concentrations in the lipid bilayer are optimal to obtain these improved physiochemical attributes.

For example, in developing the inventive commercial and improved formulation composition, the inventors evaluated two different concentrations of phytosterol inclusion concentrations, namely, 0.066% and 0.132% wt/wt. The formulation containing a concentration of 0.066% provided BHI values that were always higher than those observed for the same composition with an even higher phytosterol concentration. The inventors therefore concluded that the final sterol additive concentration of about 0.066% provided the optimal concentration for the liposomal preparation's desired physiochemical characteristics. This range can vary depending on circumstances at about 5% to 10%.

About the Particle Size

There is evidence that indicates that in liposome-based drug applications the smaller the liposome the better absorbed the drug becomes at the intestinal level. In the past these liposome-based drug preparations generally involve differing chemical bonding schemes to attach the drug to the liposome wall. However, in this example, electrolytes are instead incorporated passively in the liposome (not chemically bound to a liposome's membrane wall) encapsulation system along with other active ingredients. This is the case in the inventive liposomal formulation of electrolyte salts. The inventors observed that, unlike liposome-based drug delivery systems, in the passive liposomal delivery system of the instant invention, smaller liposomes particles encapsulated smaller volumes of electrolyte encapsulation than similar liposomes of larger size. Thus in order to prepare a commercially viable high performance liposomal encapsulated electrolyte delivery system, the inventors had to optimize the particle sizing both from a pure size perspective, and importantly, in a narrow particle size range so that all the particles in the resulting narrow particle size range would be effective. It is also known that larger diameter liposomes are far less stable and thus more prone to stress related collapse. Thus in the case of this passive electrolyte encapsulation development, the inventors learned that very large and very small liposomes must be avoided, while at the same time narrow particle size distributions are highly desirable when such delivery systems can also incorporate relatively high levels of electrolyte incorporation. These were the challenges associated with the development of the improved formulation of the instant invention.

To evaluate this point, the inventors developed formulations for the BHI tests described below, with the same composition but with varying average liposome particle sizes, namely, 160 nm and 280 nm in diameter respectively. Surprisingly in all the evaluated cases, a higher BHI value was obtained when the average particle size was about 280 nm, while the BHI obtained from average particles sizes of 180 nm provided poorer BHI results. This observation was counter-intuitive when compared to observations derived from liposomal drug delivery based system development. This led to the speculative conclusion that the lower intestinal absorption of the 160 nm particles, compared to those of 280 nm particles, may be based on compensation for and overcome by a greater incorporation of electrolyte salts in the higher particle size case despite the apparent increase in total liposomes available in the lower particle size range. Alternatively, the observation may be related to optimal particle sizing and gastrointestinal lining transport demands.

Osmolarity

The World health Organization (WHO) has issued guidelines for the desired range of osmolality desired in oral rehydration solutions in order to avoid hyper or hypotonicity reactions to these formulations which would otherwise result in undesirable side effects. Currently the available information suggests that such products must present total osmolality of 230 and 250 mOsmol/L. In liposome electrolyte encapsulated formulations encapsulated electrolytes do not contribute to global osmolality. Thus the inventors decided to evaluate two formulations with different osmolarities, namely, 190-200 mOsmol/L and 240-250 mOsmol/L where the difference in the formulations was based solely on the amount of added glucose. This difference between the two formulations was based on glucose concentrations of about 0.65% in the case of low osmolality and about 1.60% in the case of high osmolality respectively. Testing revealed that the formulation of lower osmolality was the one that provided the higher values of BHI in side by side BHI testing. Since the only difference between the two test development formulations was the amount of glucose present and since the resulting lower osmolality product provided the better BHI response, the inventors concluded that, despite the known enhancement of electrolyte transport by the use of higher levels of glucose in the presence of non-liposomed electrolytes, that the inventive product must have a different mode of action than the simple commercially available Oral Rehydration Solution (ORS) that do not contain liposomes and rely instead on enhanced electrolyte transport via active glucose-base electrolyte transport. The result of this experimental effort resulted in a high performance liposome-based ORS with low osmolality and low glucose levels when compared to the currently available non-liposomed ORS products available in the market today. Furthermore the instant formulation outperformed the existing commercial ORS products in standard human BHI clinical trials.

Improved Method of Manufacturing High Electrolyte Encapsulated Oral Rehydration Mixtures Via Initial Formation of Large Multi-Lamellar Liposomes and Their Conversion to Uni-Lamellar Vesicles The following new and improved method of manufacture and its resulting product relies on the initial formation of large multi-lamellar vesicles in the presence of substantially greater amounts of total phospholipids and lyso-phospholipids (amounting to a total content of about 0.396% in the final product of Step 6 described below) and an additional total content of total plant-based phytosterols and their respective esters (amounting to about 0.066% in the final product of Step 6 described below). These initially formed large multi-lamellar vesicles are subsequently converted to uni-lamellar vesicles (liposomes) using a high pressure extruder and the resulting liposomed mixture is adjusted to a pH of 3.9-4.1 using a 50% aqueous solution of citric acid to ensure protonation of all available choline moieties.

The new and improved product is characterized by a tight particle size distribution <400 nm (<0.4 microns), high levels of liposome electrolyte encapsulation (55-70%), low levels of carbohydrates, improved human taste acceptance and exceptional performance in a standardized human Beverage Rehydration Index clinical trial when compared to other commercial non-liposomed electrolyte products such as Pedialyte®, a product made to the specifications of and in all ways similar to Dioralyte® (the leading non-liposome based oral rehydration solution sold in the EU), as well as the disclosed prior art liposomed electrolyte products of Mitchell et al. Thus the new and improved process resulted in substantially different physiochemical characteristics and improved human Beverage Hydration Index (BHI) performance than that of Mitchell's and all other commercial oral rehydration products included in the clinical trial.

Step 1: An aqueous solution of electrolytes was prepared by adding in a flask 2.08 gm of potassium citrate, 2.65 gm of sodium chloride, 1.0 gm of sodium citrate and 17.25 gm of water with stirring until a solution is formed.

Step 2: In a separate flask, 0.66 gm of hydrogenated soy phosphatidyl choline, 3.30 gm of Phospholipon® 90G (a commercial mixture of phosphatidylcholine and lyso-phosphatidylcholine), 0.66 gm of Vegapure® 95FF (a commercial mixture of >97% free and esterified plant-based sterols) and optionally 2.5 gm of ethanol were heated and mixed to obtain a homogeneous solution. The homogeneous mixture of phospholipids, lyso-phospholipids and plant based sterols were then added slowly to the Step 1 aqueous electrolyte solution with vigorous stirring and heated at 50-60° C. The resulting liposomes formed were large multi-lamellar vesicles (liposomes). Approximately 33% of the electrolyte used in Step 1 was found to be entrapped in the resulting multi-lamellar vesicles so formed based on a comparison of the measured electrical conductivity of the same composition without liposomes present (i.e. no phospholipid or plant-based sterols added).

Step 3: The resulting warm aqueous mixture of multi-lamellar vesicles from Step 2 above was then subjected to multiple passes through a high pressure extruder which converted the multi-laminar vesicles to uni-lamellar vesicles. The mixture was allowed to slowly cool to room temperature with gentle stirring (a small amount of aqueous sucrose may be optionally added to the extruder to recover substantially all of the liposomal product at this scale). The final weight of this Step 3 mixture was 29.0 gm.

Step 4: All 29.0 gm of the resulting Step 3 uni-lamellar vesicle mixture were then poured with gentle mixing into an aqueous mixture of 6.5 gm of glucose, 5.56 gm of natural orange flavoring, 0.32 gm of stevia, 0.91 gm of sodium benzoate and 0.2 gm of artificial orange color dissolved in approximately 900 gm of water. The resulting uni-lamellar vesicle mixture had an orange-white milky opaque appearance.

Step 5: The pH of the resulting Step 4 mixture was then adjusted by adding an adequate amount of a 50% solution of citric acid to bring the pH of the Step 4 mixture to a final pH of 3.9-4.1. Then adequate water was added to bring the total weight of the resulting mixture to 1000 gm. The composition was suitable for immediate use as an oral rehydration mixture (ORS) or could be further pasteurized and stabilized for shelf stability per Step 6 below.

Step 6: The Step 5 mixture was pasteurized for 30 seconds at 180 F before bottling and providing a shelf life of 18 to 24 months. Alternatively 0.910 gm/l of Sodium Benzoate as preservative can be added to the mixture prior to pasteurization to increase shelf life for up to 36 months. The pasteurized product so prepared was used in a subsequent human clinical trial as described more fully below after product characterization.

Measured Outcomes

Osmolarity Level: The resulting liposomed final product had a calculated osmolarity of 286 mOsmol/L, and a measured osmolality of 289 mOsmol/kg using a freezing point depression method osmometer (50 it samples, MicroOsmette, Precision Systems, Inc.) and a 200 mOsmol/L using a vapor pressure method osmometer (50 µl samples, Vapro Model 5520).

Encapsulation Estimate: The Step 2 product measured osmolality indicated an encapsulation level increase from 33% in the Step 1 product to 60-68% in the final Step 2 product, as per the difference between freezing point and vapor pressure osmolarity readings, on a composition containing 130.1 mmol/L of ions. Since the vapor pressure method does not read encapsulated ions osmolarity contributions, (based on the difference between 289 mOsmol/L and 200 mOsmol/L). The inferred encapsulation level was 68% ([289-200]/130.1).

Particle Size Distribution: A narrow particle size distribution was obtained via DLS instrumentation between 225 and 350 nm (0.25-0.35 microns).

Stability: The product of Step 6 was found to be stable in accelerated stability testing protocols for at least 12-18 months when stored in bottles following pasteurization.

Final Product Composition

| | Ingredient | Percentage | g/L | Calculated Osmolality (mOsm/kg) |
|---|---|---|---|---|
| 1 | Purified water | 95.612% | 956.124 | 5 |
| 2 | Saccharose (sucrose) | 0.000% | 0.000 | 0 |
| 3 | Dextrose (glucose) | 0.650% | 6.500 | 36 |
| 4 | Citric acid | 0.473% | 4.730 | 16 |
| 5 | Nat. flavor pineapple met002877 | 0.432% | 4.320 | 16 |
| 6 | Nat. sweet and juicy orange or-42701 | 0.081% | 0.810 | 4 |
| 7 | Nat. tangerine ta-18864 | 0.041% | 0.410 | 2 |
| 8 | Monk fruit powder flavoring | 0.002% | 0.020 | 3 |
| 9 | Color red 40 | 0.001% | 0.005 | 2.5 |
| 10 | Color yellow 5 | 0.001% | 0.010 | 5 |

-continued

| | Ingredient | Percentage | g/L | Calculated Osmolality (mOsm/kg) |
|---|---|---|---|---|
| 11 | Stevia extract 80% | 0.032% | 0.318 | 0.4 |
| 12 | Sodium benzoate | 0.091% | 0.910 | 12 |
| 13* | Total phase | 2.584% | 25.843 | — |
| | Purified water | 1.588% | 15.880 | 0.1 |
| 14 | Hydrogenated soy phosphatidylcholine (HSPC) | 0.066% | 0.660 | 0 |
| 15 | Phospholipon 90G | 0.330% | 3.300 | 39 |
| 16 | Phytosterols | 0.066% | 0.660 | 0 |
| 17 | Sodium | 0.127% | 1.266 | 55 |
| 18 | Potassium | 0.075% | 0.752 | 19.3 |
| 19 | Citrate | 0.075% | 0.748 | 10.5 |
| 20 | Chloride | 0.161% | 1.607 | 45.3 |
| 21 | Sucrose | 0.027% | 0.270 | 0.8 |
| 22 | Ethanol | 0.070% | 0.700 | 18 |
| | TOTAL | 100.00% | 1,000.0 | 290 |

*Row 13 represents the total liposomal phase and is a part of the total 100% calculation, therefore it is not used in reaching the 100% number.

| Composition Attributes | |
|---|---|
| Type of Phospholipids | Hydrogenated soy phosphatidylcholine (HSPC) and Phospholipon 90G |
| Number of different types of phospholipids | 2 |
| % of Phospholipids | 0.396% |
| Phospholipid Average Size | <270 nm |
| Osmolality | 200 mOsmol/kg based on measured Vapor Pressure |
| % of Glucose | <0.7% |
| % of Total Carbohydrates | <0.7% |
| Calories per L | ~27 |
| Encapsulation Level | <68% |
| Product Stability | 6 months stability at 25 degrees Celsius |
| Product Taste | Similar to a Gatorade |
| Sodium mEq/L | 55 |
| Total Ions mg/L | <4,400 |
| pH | <3.7 |
| Brix | 2.5 |
| Type of liposomes | Uni-lamellar Vesicles |

These values can range over a wide range depending on end use requirements and manufacturing, as reflected in the range of values listed in the parent and grandparent applications.

Preparation of Liposome-Based Oral Rehydration Mixture of Mitchell
(Based on U.S. Patent Publication No. 2005/0008685 dated Jan. 13, 2005 to Mitchell et al., Examples 1 and 3)

As experts in the field of liposomal technology, the inventors attempted to reproduce the prior art Therapeutic Liposomal Electrolyte (TLEC) composition of Example 1 in Mitchell and to convert the resulting TLEC to the Ready to Drink (TORO) of Example 3 to be used as the basis for preparing a clinical comparison of the cited prior art of Mitchell in a subsequent human clinical trial. Below is a description of the development process to replicate Mitchell and its final outcome.

Step A: Prepare the initial mixture of electrolytes, water, phosphatidyl choline (0.06%) and citric acid by stirring in a helical type mechanical stirrer for 12 hours.

Step B: A 120-watt sonicator with a frequency of 40 kHz was employed for purposes of producing uni-lamellar vesicles according to Example 1 and per the literature references cited in the patent application. The sample was kept under these conditions for 10 minutes and a sample was taken to measure the resulting particle size via Dynamic Light Scattering (DLS).

Step C: Sonication was continued for another ten minutes and then a second sample was taken to measure particle size via DLS.

Step D: Sonication was then continued for a total of 90 minutes (total energy employed 180 watts), obtaining the third sample to calculate and measure the osmolarity, estimate the encapsulation level and measure particle size via DLS.

Step E: in 970 mL of water add Sucrose, Glucose, Maltodextrin, and Citric Acid as per disclosures, and dissolve completely in agitation.

Step F: Add liposomal dispersion into the previous solution.

Step G: Add indicated amount of flavoring and agitate.

Step H: Dilute to final volume of with distilled water while stirring.

The following outcomes for prior art Mitchell's mixture were observed:

Osmolality Level: Mitchell's disclosed osmolality level was <400 mOsm/kg noted in its claim 1. The Step D sample calculated osmolality value was 315 (174 mOsmol/kg due to the contribution to osmolarity from free ionic electrolytes and 130 mOsmol/Kg due to the contribution to osmolarity from sugars) while the measured osmolality via the vapor pressure method reading was <300, thus the sample met Mitchell's osmolality disclosure.

Encapsulation Level: Mitchell's disclosed volume inclusion was ≥25%. In the inventors' replication of Mitchell's Example 1 TLEC, the inventors estimated an encapsulation level, based on measured osmolarity, of approximately 30%, thus the sample met Mitchell's disclosed encapsulation level.

Particle Size: Mitchell's claimed a particle size achievement of all particles <500 nm (<0.5 microns). In the inventors' attempted replication, even after 90 minutes of high energy sonication, the inventors were not able to obtain Mitchell's stated particle size but instead obtained particles as small as 700 nm (0.7 microns lower end of PSD) as measured by DLS (Mitchell does not disclose the method employed to measure particle size distributions in Example 1, thus the comparison is likely not a valid one between the two clinical samples. Accordingly to the resulting TLEC as per Mitchell was added tapioca syrup solids, flavor, sucralose, pectin, color and water to obtain 1000 gm (1 liter) of mixture for use as a comparator in a human clinical trial.

| Mitchell's Therapeutic Oral Rehydration Solution | | | |
|---|---|---|---|
| Ingredient | gm/l | % | TLEC Concentration |
| potassium chloride | 1.484 | 0.15% | 5.30% |
| sodium chloride | 2.6012 | 0.26% | 9.29% |
| trisodium citrate dihydrate | 2.9176 | 0.29% | 10.42% |
| phosphatidyl choline | 0.56 | 0.06% | 2.00% |
| Antioxidant (mixed Tocopherol) | 0.0392 | 0.00% | 0.14% |
| Antioxidant (Citric Acid) | 0.014 | 0.00% | 0.05% |
| water | 20.384 | 2.04% | 72.80% |
| Total TLEC | 28 | 2.80% | 100.00% |
| Complex carbohydrates (Tapioca Syrup Solids) | 40 | 4.00% | |
| Flavor | 3.5 | 0.35% | |
| Sucralose, dry | 0.075 | 0.01% | |
| Pectin, dry | 0.45 | 0.05% | |

-continued

Mitchell's Therapeutic Oral Rehydration Solution

| Ingredient | gm/l | % | TLEC Concentration |
|---|---|---|---|
| Color, dry | 0.033 | 0.00% | |
| Water | 927.942 | 92.79% | |
| TOTAL TORC Ready to Drink | 1000 | 100.00% | |

| Composition Attributes | Actual | Patent Claim |
|---|---|---|
| Type of Phospholipids | Phospholipon 90G | |
| Number of different types of phospholipids | 1 | |
| % of Phospholipids | <0.06% | |
| Phospholipid Average Size | >700 nm | <500 nm |
| Osmolality | 260 mOsmol/kg based on Vapor Pressure method | <300 |
| % of Glucose | 1.50% | |
| % of Total Carbohydrates | 4% | |
| Calories per L | 160 | |
| Encapsulation Level | <30% | >25% |
| Product Stability | Undetermined | |
| Product Taste | Worse than Pedialyte | |
| Sodium mEq/L | 76 | |
| Total Ions mg/L | >7000 | |
| pH | | |
| Brix | | 76-85 |
| Type of Liposomes | Unilamellar spheres liposomes | |

When comparing the new and improved liposome based formulation of the invention with that of Mitchell's ready to drink (RTD) TORS product, the following differences are noted:

1) Contains 7× more phospholipids than Mitchell's TORS RTD product.

2) Contains two differing phospholipids, namely Phosphatidylcholine and Lyso-Phosphatidylcholine, whereas Mitchell's product only included the former and in far lower amounts.

3) Contains plant-based sterols and their esters while Mitchell's TLEC and TORS products contains none.

4) Contains just 6.5 g/L (0.65%) of glucose, 0.27 g/L of sucrose (0.027%) and 0.32 g/L (0.032%) of Stevia natural sweetener compared to Mitchell's TORS RTD product which contains 40.45 g/L (4.45%) (6× more) of complex carbohydrates and the artificial sweetener sucralose.

5) The inventors' formulation had a measured particle size distribution (PSD) that is in a far tighter range between 225-350 nm, while Mitchell's TORS RTD product PSD range was disclosed to be to be <500 nm (0.5 microns).

6) Exhibits a far higher total liposomal electrolyte inclusion volume (60-68%) than Mitchell's 25% liposomal electrolyte inclusion volume TORS RTD product.

7) Does not include complex carbohydrates like Mitchell's TORS RTD product.

8) Exhibits a lower osmolality of 200 mOsmol/L than Mitchell's TORS RTD product which was observed to be about 260 mOsmol/L.

9) Contains total dissolved solids of just 28 g/L versus a total dissolved solids content in Mitchell's TORS RTD product of 48.8 g/L.

10) Exhibits a lower pH than Mitchell's TORS RTD product which pH adjustment was not conducted in any of Mitchell's Examples section.

11) The new product has a caloric value of just 35 Kcal/L versus the Mitchell TORS RTD product which has a caloric value of 178.5 Kcal/L making the new product more compatible for use with diabetics.

12) The new process starts by manufacturing a mixture containing multi-lamellar vesicles which in a separate step are subsequently converted to stable uni-lamellar vesicles in the final product while the Mitchell process relies on a single step uni-lamellar process.

13) The product of the invention is more palatable than Mitchell's TORS RTD product.

14) The pasteurized new product of the invention is stable for extended periods of time in bottled storage containers and thus does not require removal of water as in the cited prior art.

15) In human clinical trials the new product of the invention far outperformed Mitchell's TORS RTD product in net fluid retention.

16) The new and improved product represents a superior hypotonic electrolyte delivery system for the treatment of a wide range of electrolyte disorders in humans.

Clinical Background

Acute gastroenteritis accounts for 3-5 billion cases a year and nearly 2 million deaths occur each year in children under 5 years across the world. See Elliott, "Acute Gastroenteritis in Children," BMJ; 2007.

Apart from gastroenteritis, around 60 million people are affected by some kind of digestive disorder in the US. See Steiner et al., "Is This Child Dehydrated?" JAMA; 2004; Digestive Diseases Statistics for the United States, National Institute of Diabetes and Digestive and Kidney Diseases.

Across the US, Norovirus illness alone causes 21 million cases of acute gastroenteritis that accounts for 1.7 million outpatient visits a year, 800 deaths and $2 billion costings. See "Burden of Norovirus Illness in the U.S.," Center for Disease Control, https://www.cdc.gov/norovirus/trends-outbreaks/burden-US.html.

Dehydration may be associated with electrolyte disturbance and metabolic acidosis which could be the most frequent as well as dangerous type of complications. However, optimal management of these complications with the help of oral or IV fluids could minimize the risk of dehydration and its adverse outcomes.

The Beverage Hydration Index (BHI) is a new human metric that identifies the short-term hydration potential of a particular beverage as well as its ability to maintain a hydration status for a comparatively long period of time which could avoid adverse outcomes.

A new oral rehydration mixture (ORM) formulation containing salts encapsulated in liposomes which can mediate the uptake of electrolytes by alternative modes of action to glucose-mediated transporters may lead to a timely release and better absorption of the salts. This may lead to a higher BHI as compared to the conventional hydration ORS as well as developing an improved patient compliance for a more pleasant drink.

Methods

In a blind cross-over which involved the comparative live study, 10 male adults (18 to 45 years) were administered with four test drinks. The study was conducted for a period of six months.

The participants emptied their bladders upon waking up after an overnight fast of at least 8 hours. One hour before arriving at the laboratory, the volunteers consumed 500 mL of still water over the course of 15 minutes.

Upon arrival in the laboratory, participants were asked to void their bowels and bladder before the measurement of their near-nude body masses (underwear only) to the nearest 50 g.

Participants then ingested 1 L of the assigned test drink over a period of 30 minutes (4 equal volumes administered between 7.5 minutes).

The participants were asked to empty their bladders after the drinking period was over (time 0) and then again at the end of each hour in the study period. After the final urine samples were collected, the near-nude body masses were recorded again.

Test drinks included market leader ORS product Pedialyte, high sodium and low osmolality ORS which is similar to Dioralyte, low size liposome particles with high encapsulation level and low osmolality liposomal ORM, and high sodium with medium sized particles and lower electrolyte encapsulation level liposomal ORM.

All of the drinks were tested for osmolality, sodium and potassium.

Aim

Determination of the beverage consisting of the highest BHI potential in order to avoid/limit the use of IV fluids when possible.

Clinical results are shown in FIGS. 3-6.

Results

Four hours after the ingestion of the test drinks, cumulative urine mass was lower and net fluid balance were higher as compared to water only in the formulation of low osmolality liposome ORS with $p<0.005$ and $p<0.05$, respectively. In absolute terms, the net fluid balance of this formula was over five times higher than the following test fluids (−30 grams vs. −167 grams in Pedialyte), though with $p<0.25$ due to small group size.

After 2 hours of ingestion, the low osmolality liposome ORS presented the highest BHI value (1.47) with an effect size of more than one standard deviation from the second highest BHI value (Pedialyte $p<0.06$) and showed the largest deviation when compared to water ($p<0.0002$).

After 2 hours of ingestion, the low osmolality liposome ORS resulted as the only formulation having net fluid absorption of 150 grams from the one liter ingested.

Discussion of Results

Figure 3:
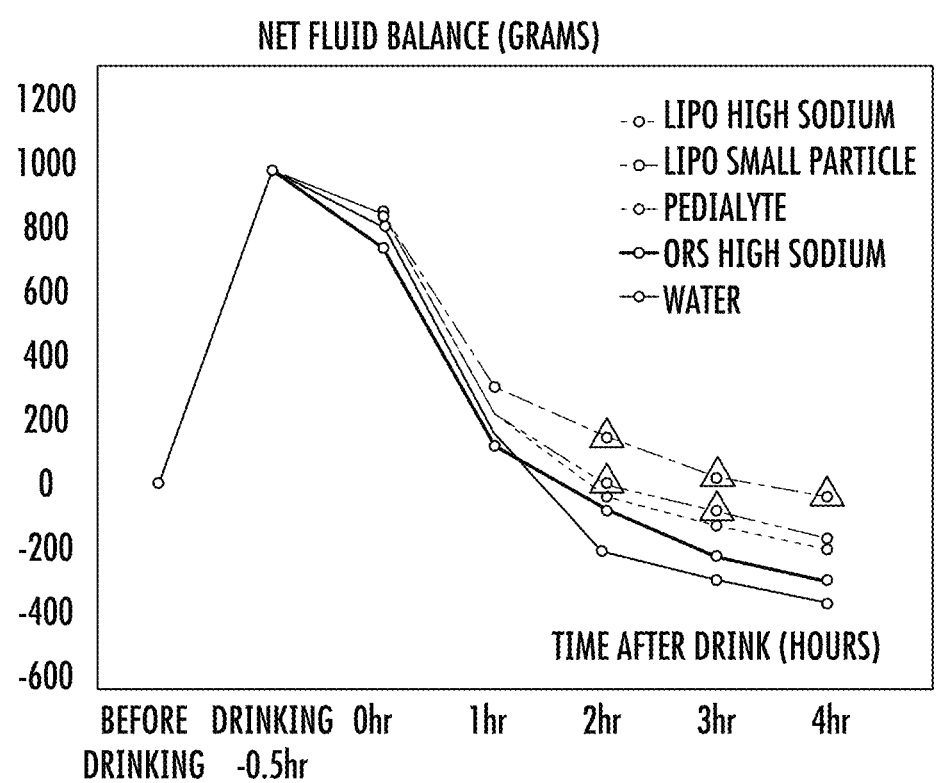
FIG. 3 is a graph showing cumulative volume of urine (grams) passed over a fixed period of 4 hours after the ingestion of 1 liter of each drink where drinks with different responses to still water were identified by paired t-test analysis at each time point and were highlighted in the triangular boxes for $p<0.05$.

FIG. 3 shows the cumulative urine output over time for each clinical arm and indicates that only the Inventive Product and Pedialyte® resulted in a significant volume difference over the water arm.

Figure 4:
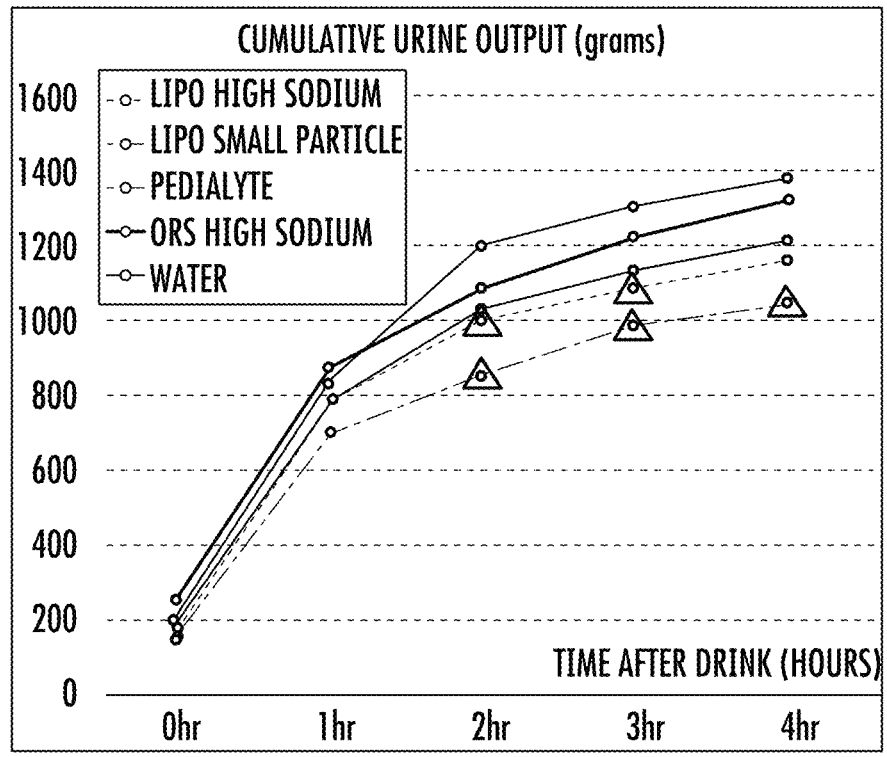
FIG. 4 is a graph showing net fluid balance after ingestion of 1 liter of each drink where drinks with different responses to still water were identified by paired t-test analysis at each time point and highlighted in the triangular boxes for $p<0.05$.

FIG. 4 indicates the net fluid balance during the clinical trial and indicates that only the Inventive Product and Pedialyte® arms provided statistically significant differences over the water control. Interestingly, even at the 4 hour test point the Inventive Liposome-based Product was over 5× more effective than Pedialyte in Net Fluid Balance Retention having lost only 30 grams of fluid while the Pedialyte formula had lost 167 grams of fluid and the prior art liposome-based product lost 209 grams of fluid.

Figure 5:
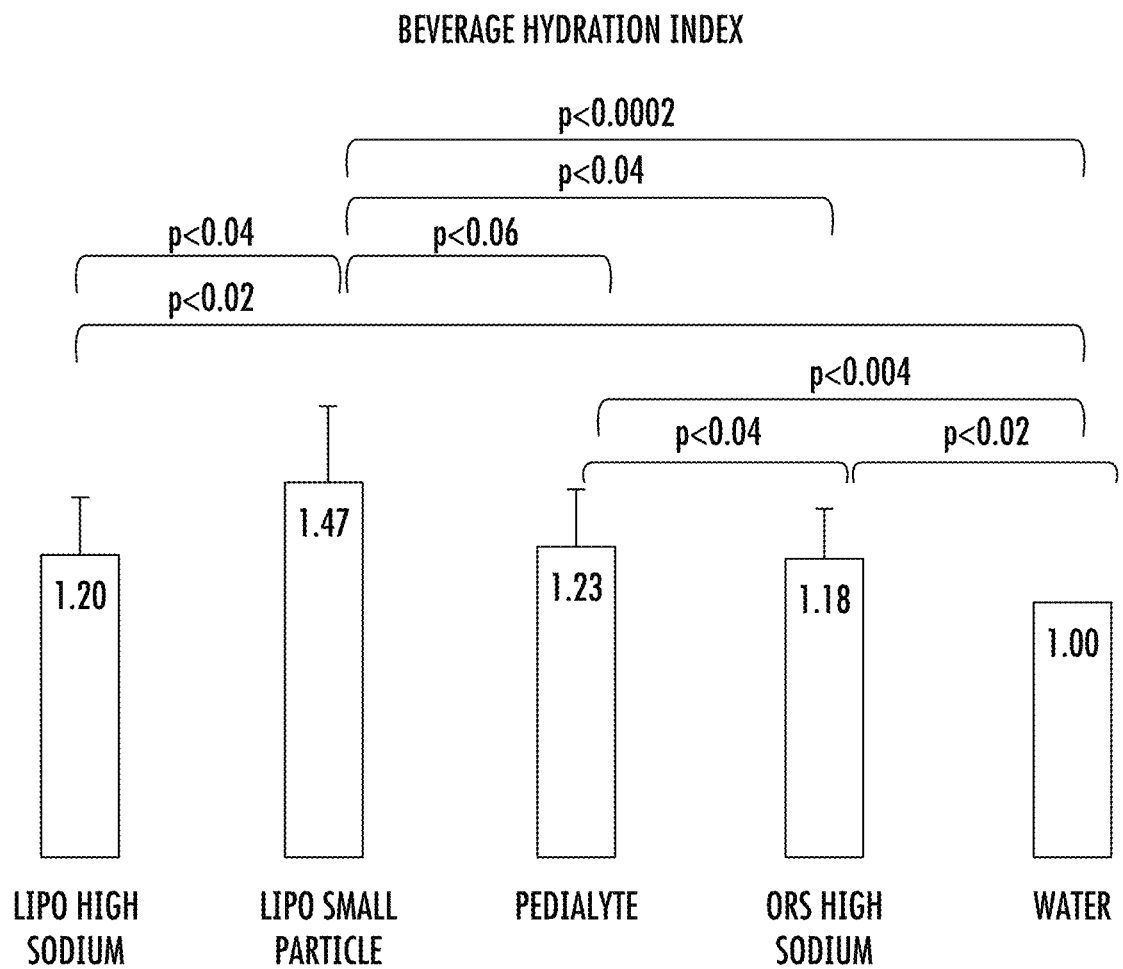
FIG. 5 is a chart showing BHIs for the ORS standard of care and liposomal ORS formulas where drinks were identified by the paired t-test analysis against each other for $p<0.05$.

FIG. 5 indicates that the highest BHI was obtained by using the Product of the Invention (BHI=1.47) which outperformed the Mitchell product (BHI=1.20) as well as Pedialyte® (BHI=1.21) and the Dioralyte® similar (BHT-1.18). In this clinical trial as expected the water control exhibited a BHI=1.0. The inventors can conclude that the liposome based Mitchell product was no better in raising the BHI than the commercially available non-liposome based product Pedialyte® or the non-liposomed product Dioralyte® similar.

Figure 6:
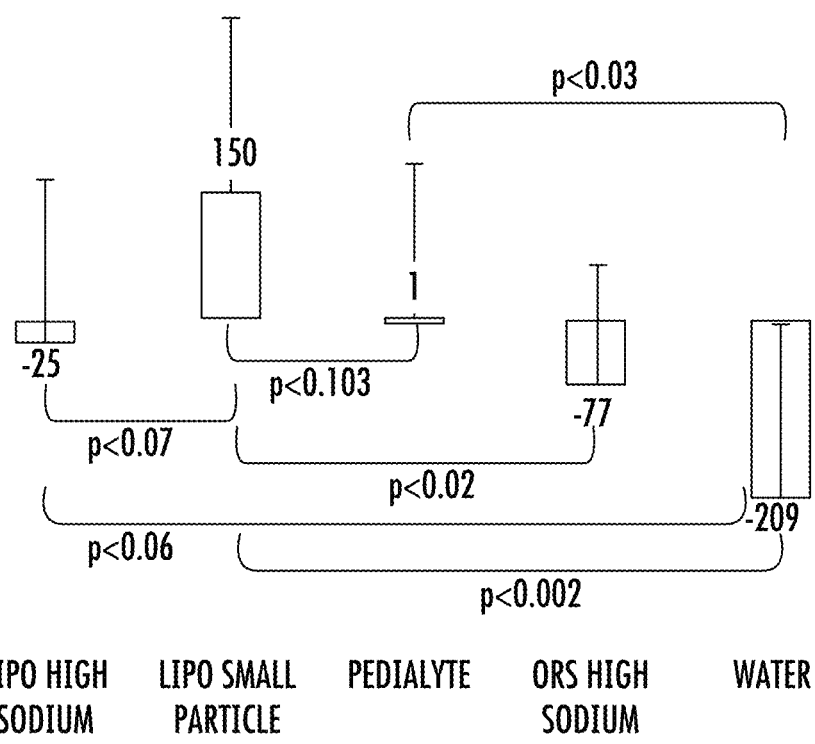
FIG. 6 is a chart showing net fluid absorption after 2 hours of ingestion of 1 liter of each drink where drinks were identified by paired t-test analysis against each other for $p<0.11$.

FIG. 6 indicates net fluid absorption (i.e. Net Fluid Retention) at the critical 2 hour assessment point and indicates that the Inventive Product outperformed all other arms while providing the only statistically significant and positive fluid absorption (retention) of 150 ml among the various arms of the clinical study.

Four hours after the ingestion of the test drinks, cumulative urine mass was lower and net fluid balance was higher as compared to water only in the formulation of low osmolality liposome ORS with $p<0.005$ and $p<0.05$, respectively. In absolute terms, the net fluid balance of this formula was over five times higher than the following test fluids (−30 grams vs. −167 grams in Pedialyte), though with $p<0.25$ due to small group size.

After 2 hours of ingestion, the Inventive low osmolality liposome ORS presented the highest BHI value (1.47) with an effect size of more than one standard deviation from the second highest BHI value (Pedialyte $p<0.06$) and showed the largest deviation when compared to water ($p<0.0002$).

After 2 hours of ingestion, the low osmolality liposome ORS of the invention was the only formulation having net fluid absorption (retention) of 150 grams from the one liter of water ingested.

Conclusion

In a definitive human blinded cross-over clinical study, the Inventive Liposome-based Product proved to be far superior in Net Fluid Absorption and provided the highest Beverage Hydration Index (BHI) when compared to the closest prior art liposome-based product (Mitchell et. al.) as well as two standard of care commercially available non-liposome-based oral rehydration solutions (ORS).

Overall Conclusions

A Liposomal ORS of small particles size with high encapsulation level of electrolyte contents and low osmolality leads to a more effective fluid absorption in the BHI when compared to the other types of ORS formulation, even to formulas with 36% more sodium.

Low osmolality liposomes may provide an additional path for sodium absorption, less dependent pathways for glucose co-transport and possesses extremely low carbohydrate contents which may make it quite relevant for vast populations and their needs of low glucose content.

For individuals that require rapid hydration and long-term maintenance of fluid balance or experience difficulty in complying with the large drinking quantities, low osmolality liposome ORS proves to be the best hydration alternative to absorb as well as retain fluid for a longer period of time based on the BHI.

The findings suggest that treatment with low osmolality liposomal formulations may reduce the need for the administration of intravenous solutions. This is particularly relevant for communities with limited access to intravenous fluid or when there is a significant shortage of IV bags during natural catastrophes and emergencies.

Many modifications and other embodiments of the invention will come to the mind of one skilled in the art having the benefit of the teachings presented here and the associated drawings. Therefore, it is understood that the invention is not to be limited to the specific embodiments disclosed, and that modifications and embodiments are intended to be included within the scope of the appended claims.

That which is claimed is:

1. An acidic, ready-to-drink, oral, liposome based, hypotonic electrolyte rehydration composition that is shelf-stable for 12 to 18 months, comprising at least about 95% water, salts and phospholipid liposome particles and having a phospholipid concentration of about 1.0 g/L to 10.0 g/L, said phospholipid liposome particles comprising a phospholipid bi-layer having incorporated sterols therein, and a concentration of the incorporated sterols up to about 0.132% wt/wt, and a phospholipid particle diameter size between about 225 nm and 350 nm, wherein at least 50 percent of the total salts present in the rehydration composition are encapsulated within the phospholipid liposome particles, and a sodium electrolyte concentration of about 12 mmol/L to about 90 mmol/L, wherein the composition has an actual osmolality lower than 260 mOsm/kg measured via a vapor pressure osmometer, a carbohydrate concentration less than 4% and without complex carbohydrates, and a Beverage Hydration Index (BHI) above 1.20.

2. The composition of claim 1 wherein the incorporated sterols comprise a plant based phytosterol at about 0.066% to about 0.132% wt/wt.

3. The composition of claim 1 wherein the composition includes citric acid in an amount to give the composition a pH of about 3.9 to 4.1.

4. The composition of claim 1 wherein the total carbohydrate concentration is less than about 0.7%.

5. The composition of claim 1 wherein the phospholipids consist of hydrogenated soy phosphatidylcholine and phospholipon 90G.

6. The composition of claim 1 wherein about 60% to about 68% of the total salts within the composition are encapsulated within the phospholipid liposome particles.

7. The composition of claim 1 wherein the sodium electrolyte concentration is about 35 mmol/L to about 55 mmol/L, and further comprising a potassium electrolyte having a concentration of about 15 mmol/L to about 25 mmol/L.

8. A method of preventing dehydration and maintaining body electrolytes and fluids in a human, or rehydrating a human suffering from dehydration, comprising orally administering an acidic, ready-to-drink, oral, liposome based, hypotonic electrolyte rehydration composition that is shelf-stable for 12 to 18 months, comprising at least about 95% water, salts and phospholipid liposome particles and having a phospholipid concentration of about 1.0 g/L to 10.0 g/L, said phospholipid liposome particles comprising a phospholipid bi-layer having incorporated sterols therein, and a concentration of the incorporated sterols up to about 0.132% wt/wt, and a phospholipid particle diameter size between about 225 nm and 350 nm, wherein at least 50 percent of the total salts present in the rehydration composition are encapsulated within the phospholipid liposome particles, and a sodium electrolyte concentration of about 12 mmol/L to about 90 mmol/L, wherein the composition has an actual osmolality lower than 260 mOsm/kg measured via a vapor pressure osmometer, a carbohydrate concentration less than 4% and without complex carbohydrates, and a Beverage Hydration Index (BHI) above 1.20.

9. The method according to claim 8 wherein composition is formulated for oral administration for use by humans that are pregnant or breast-feeding or engaged in sport exercises or outdoor activities.

10. The method according to claim 8 wherein the composition is formulated for oral administration for use by patients having one or more of stomach ailments, skin burns, parenteral or enteral nutrition ailments, celiac disorders, diabetes, SGLT2 inhibitor treatment disorders, intestinal failure, Short Bowel Syndrome, Cycling Vomiting Syndrome, Gastroparesis, Postural Orthostatic Tachycardia Syndrome, Ulcerative Colitis, Colon Cancer, Dysphagia, Sjogren Syndrome, Crohn's disease, Lupus, Alzheimer's disease, Renal complications, HIV, Inflammatory Bowel Disease, an Ostomy, Microvillus Inclusion Disease, and Cystic Fibrosis.

11. The method of claim 8 wherein the incorporated sterols comprise a plant based phytosterol at about 0.066% to about 0.132% wt/wt.

12. The method of claim 8 wherein the composition includes citric acid in an amount to give the composition a pH of about 3.9 to 4.1.

13. The method of claim 8 wherein the total carbohydrate concentration is less than about 0.7%.

14. The method of claim 8 wherein the phospholipids consist of hydrogenated soy phosphatidylcholine and phospholipon 90G.

15. The method of claim 8 wherein about 60% to about 68% of the total salts within the composition are encapsulated within the phospholipid liposome particles.

16. The method of claim 8 wherein the sodium electrolyte concentration is about 35 mmol/L to about 55 mmol/L, and further comprising a potassium electrolyte having a concentration of about 15 mmol/L to about 25 mmol/L.

17. A method of forming a ready-to-drink, oral liposome based, hypotonic electrolyte rehydration composition that includes at least about 95% water, salts and phospholipid liposome particles and having a phospholipid concentration of about 1.0 g/L to 10.0 g/L, the phospholipid liposome particles comprising a phospholipid bi-layer having incorporated sterols therein, and a concentration of the incorporated sterols up to about 0.132% wt/wt, and a phospholipid particle diameter size between about 225 nm and 350 nm, wherein at least 50 percent of the total salts present in the rehydration composition are encapsulated within the phospholipid liposome particles, and a sodium electrolyte concentration of about 12 mmol/L to about 90 mmol/L, wherein the composition has an actual osmolality lower than 260 mOsm/kg measured via a vapor pressure osmometer, a carbohydrate concentration less than 4% and without complex carbohydrates, and a Beverage Hydration Index (BHI) above 1.20, the method comprising:

forming a first solution of potassium citrate, sodium chloride, sodium citrate and water;

forming a second solution of hydrogenated soy phosphatidylcholine and phospholipon 90G, plant-based sterols and ethanol;

adding the second solution to the first solution at a temperature of about 50 to about 60 degrees Centigrade to form an aqueous mixture of multi-lamellar liposomes;

subjecting the aqueous mixture of multi-lamellar liposomes to multiple passes through a high pressure extruder to convert the multi-lamellar liposomes to uni-lamellar liposomes;

cooling the aqueous mixture of uni-lamellar liposomes to about room temperature;

adding the aqueous mixture of uni-lamellar liposomes into an aqueous mixture of glucose, flavoring and water to form a final liposome solution; and adding citric acid into the final liposome solution to bring the pH to about 3.9 to about 4.1.

18. The method according to claim 17 further comprising adding water to the final liposome solution and pasteurizing the final liposome solution for about 30 seconds at about 180 degrees centigrade.

19. The method according to claim 18 further comprising adding Sodium Benzoate as a preservative prior to pasteurizing the final liposome solution.

* * * * *

UNITED STATES PATENT AND TRADEMARK OFFICE
CERTIFICATE OF CORRECTION

PATENT NO. : 10,751,283 B2
APPLICATION NO. : 16/554797
DATED : August 25, 2020
INVENTOR(S) : Nicastro et al.

Page 1 of 1

It is certified that error appears in the above-identified patent and that said Letters Patent is hereby corrected as shown below:

On the Title Page

Related U.S. Application Data (Item (63)):

Delete:
"Continuation-in-part of application No. 15/797,031, filed on Oct. 30, 2017, now abandoned, which is a continuation-in-part of application No. 15/111,485, filed as application No. PCT/ES2015/070003 on Jan. 7, 2015, now abandoned."

Insert:
-- Continuation-in-part of application No. 15/797,031, filed on Oct. 30, 2017, now abandoned, which is a continuation-in-part of application No. 15/111,485, filed on July 14, 2016, which is a 371 of PCT/ES2015/070003, filed on January 7, 2015, now abandoned. --

Signed and Sealed this
Thirteenth Day of October, 2020

Andrei Iancu
*Director of the United States Patent and Trademark Office*